United States Patent
Gelfand et al.

(10) Patent No.: US 9,527,906 B2
(45) Date of Patent: *Dec. 27, 2016

(54) IMMUNOTHERAPIES EMPLOYING SELF-ASSEMBLING VACCINES

(75) Inventors: Jeffrey A. Gelfand, Cambridge, MA (US); Mark C. Poznansky, Charlestown, MA (US); Pierre R. Leblanc, Stoneham, MA (US); Svetlana E. Korochkina, Lexington, MA (US)

(73) Assignee: The General Hospital Corporation, Charlestown, MA (US)

( * ) Notice: Subject to any disclaimer, the term of this patent is extended or adjusted under 35 U.S.C. 154(b) by 521 days.

This patent is subject to a terminal disclaimer.

(21) Appl. No.: 12/988,445

(22) PCT Filed: Apr. 17, 2009

(86) PCT No.: PCT/US2009/041029
§ 371 (c)(1),
(2), (4) Date: Feb. 9, 2011

(87) PCT Pub. No.: WO2009/129502
PCT Pub. Date: Oct. 22, 2009

(65) Prior Publication Data
US 2011/0129484 A1    Jun. 2, 2011

Related U.S. Application Data

(60) Provisional application No. 61/046,195, filed on Apr. 18, 2008.

(51) Int. Cl.
| | | |
|---|---|---|
| *A61K 39/395* | (2006.01) | |
| *A61K 38/02* | (2006.01) | |
| *A61K 35/00* | (2006.01) | |
| *A61K 35/76* | (2015.01) | |
| *A61K 35/74* | (2015.01) | |
| *A61K 36/06* | (2006.01) | |
| *A61K 39/00* | (2006.01) | |
| *A61K 39/12* | (2006.01) | |
| *A61K 39/02* | (2006.01) | |
| *A61P 37/04* | (2006.01) | |
| *C07K 16/18* | (2006.01) | |
| *A61K 38/16* | (2006.01) | |
| *A61K 38/17* | (2006.01) | |
| *C07K 14/35* | (2006.01) | |
| *C07K 16/28* | (2006.01) | |

(52) U.S. Cl.
CPC ............ *C07K 16/18* (2013.01); *A61K 38/164* (2013.01); *A61K 38/1709* (2013.01); *C07K 14/35* (2013.01); *C07K 16/28* (2013.01); *C07K 2317/21* (2013.01); *C07K 2317/622* (2013.01); *C07K 2319/00* (2013.01); *C07K 2319/22* (2013.01)

(58) Field of Classification Search
None
See application file for complete search history.

(56) References Cited

U.S. PATENT DOCUMENTS

| | | | |
|---|---|---|---|
| 7,262,014 B2 | 8/2007 | Mizzen et al. | |
| 7,749,501 B2 * | 7/2010 | Gelfand | C07K 14/35 424/133.1 |
| 7,943,133 B2 | 5/2011 | Gelfand | |
| 2005/0089841 A1 * | 4/2005 | Siegel et al. | 435/5 |
| 2005/0221395 A1 | 10/2005 | Zabrecky et al. | |

FOREIGN PATENT DOCUMENTS

WO    WO-2007/136892    11/2007

OTHER PUBLICATIONS

Bowie et al (Science, 1990, 257:1306-1310).*
Greenspan et al. (Nature Biotechnology 7: 936-937, 1999).*
Laitinen, OH et al, "Brave new (strept) avidins in biotechnology," Trend, Biotechnol. 25(6):269-277 (2007).
Nordlund, HR et al, "Tetravalent single-chain avidin: from subunits to protein domains via circularly permited avidins," Biochem. J. 392:485-491 (2005).
International Search Report for PCT/US2009/041029 dated Nov. 5, 2009.
Hao et al., "HSP70 and Tumor Immunotherapy," Acta Academiae Medicinae Neimongol, 29(4):297-301 (2007).
Honghai et al., "The Research Progress of HSP70 in Tumor Immunotherapy," Chemistry of Life, 22(6):533-536 (2002).
Liu et al., "A novel therapeutic fusion protein vaccine by two different families of heat shock proteins linked with HPV16 E7 generates potent antitumor immunity and antiangiogenesis," Vaccine, 26:1387-1396 (2008).
Srivastava and Udono, "Heat shock protein-peptide complexes in cancer immunotherapy," Current Opinion in Immunology, 6(5):728-732 (1994).
Udono et al., "Heat Shock Proteins in Cancer Immunotherapy," Gann Monograph on Cancer Research, 48:201-209 (1999).
Supplementary European Search Report dated Sep. 6, 2012, from EP 09732789.4.

* cited by examiner

*Primary Examiner* — Robert A Zeman
(74) *Attorney, Agent, or Firm* — Foley Hoag LLP

(57) ABSTRACT

Provided herein are self-assembling pharmaceutical compositions comprising a heat shock protein fused to a biotin-binding protein, wherein the biotin-binding protein is non-covalently bound to four biotinylated components, and further wherein at least two of the four biotinylated components are not identical.

15 Claims, 11 Drawing Sheets

A.
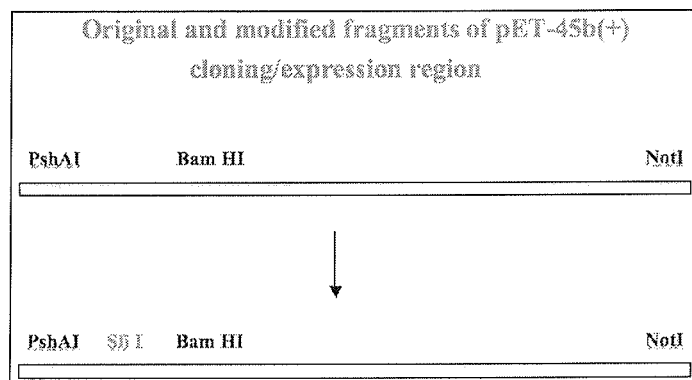
B.
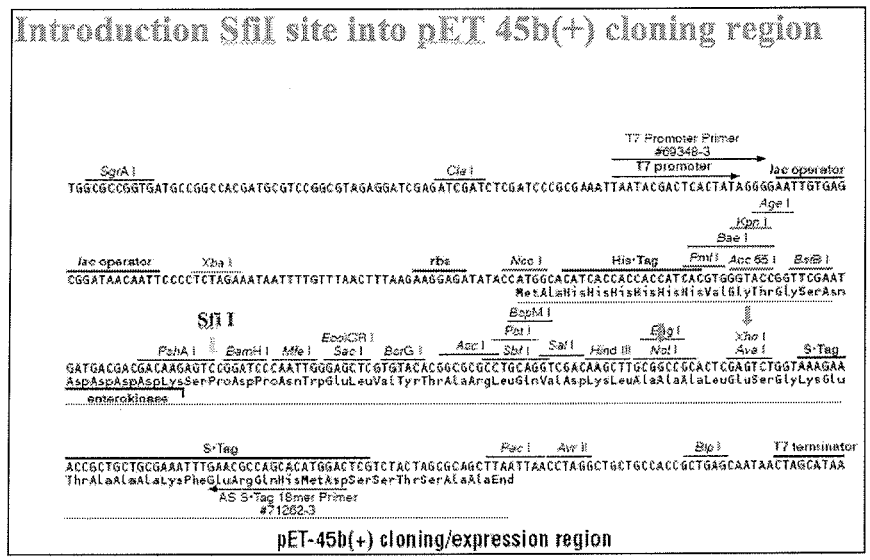
Figure 1

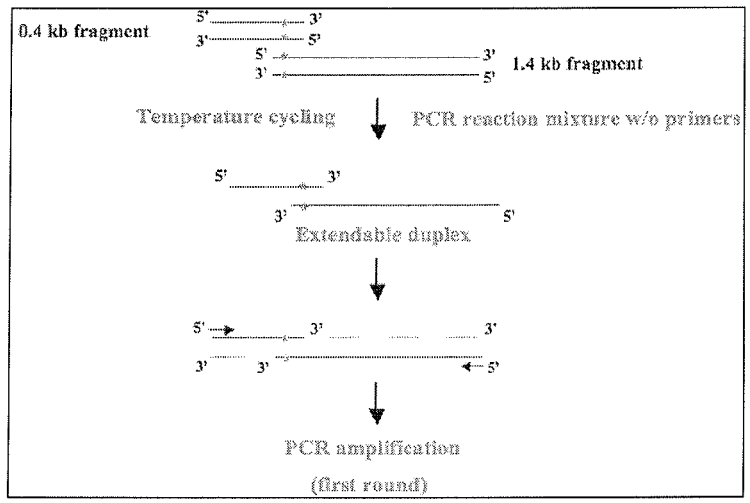
Figure 4
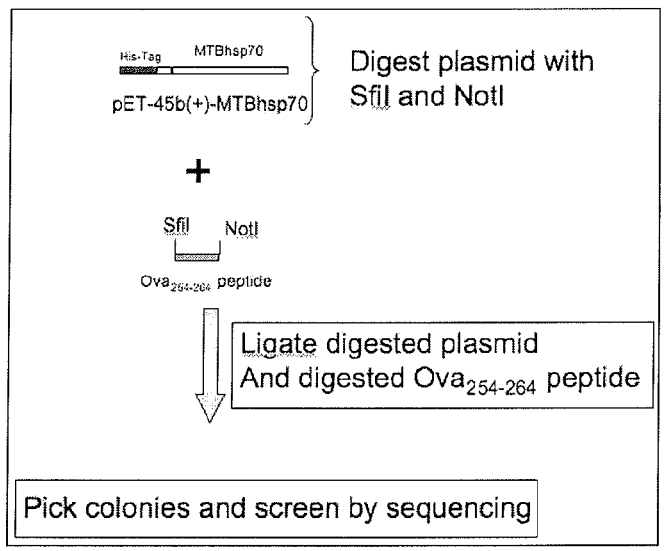
Figure 5
Figure 6

Monomeric Avidin

```
 1  M  A  R  K  C  S  L  T  G  K  W  T  N  D  L  G  S  N  M  T  I  G  A  V  N  S  R  G  E  F  T  G  I  Y
 1  ATGGCGCGTA AATGCAGCCT GACCGGCAAA TGGACCAACG ATCTGGGCTC CAACATGACC ATCGGGGCTG TGAACAGCAG AGGTGAATTC ACAGGCACCT
                                                                                              EcoRI
    Y  I  T  A  V  T  A  T  S  N  E  I  K  E  S  P  L  H  G  T  Q (A) T  I  N  K  R  T  Q  P  T  F  G  F
101 ACATCACAGC CGTAACAGCC ACATCAAATG AGATCAAAGA GTCACCACTG CATGGGACAC AAGCCACCAT CAACAAGAGG ACCCAGCCCA CCTTTGGCTT
    F  T  V (A) W  K  F  S  E  S  T  T  V  F  T  G  Q  C  F  I  D  R  N  G  K  E  V  L  K  T (A) W  L  L
201 CACCGTCGCT TGGAAGTTTT CAGAGTCCAC CACTGTCTTC ACGGGCCAGT GCTTCATAGA CAGGAATGGG AAGGAGGTCC TGAAGACCGC GTGGCTGCTG
                                                                                                    PstI
    R  S  S  V  N  D  I  G  D  D  W  K  A  T  R (A) G  I  N (A) F  T  R  L  Q  *
301 CGGTCAAGTG TTAATGACAT TGGTGATGAC TGGAAAGCTA CCGGGGCCGG CATCAACGCC TTCACTCGCC TGCAGTGA
```

Wild-type Avidin

```
 1  M  A  R  K  C  S  L  T  G  K  W  T  N  D  L  G  S  N  M  T  I  G  A  V  N  S  R  G  E  F  T  G  I  Y
 1  ATGGCGCGTA AATGCAGCCT GACCGGCAAA TGGACCAACG ATCTGGGCTC CAACATGACC ATCGGGGCTG TGAACAGCAG AGGTGAATTC ACAGGCACCT
                                                                                              EcoRI
    Y  I  T  A  V  T  A  T  S  N  E  I  K  E  S  P  L  H  G  T  Q (N) T  I  N  K  R  T  Q  P  T  F  G  F
101 ACATCACAGC CGTAACAGCC ACATCAAATG AGATCAAAGA GTCACCACTG CATGGGACAC AAAACACCAT CAACAAGAGG ACCCAGCCCA CCTTTGGCTT
    F  T  V (N) W  K  F  S  E  S  T  T  V  F  T  G  Q  C  F  I  D  R  N  G  K  E  V  L  K  T (M) W  L  L
201 CACCGTCAAT TGGAAGTTTT CAGAGTCCAC CACTGTCTTC ACGGGCCAGT GCTTCATAGA CAGGAATGGG AAGGAGGTCC TGAAGACCAT GTGGCTGCTG
                                                                                                    PstI
    R  S  S  V  N  D  I  G  D  D  W  K  A  T  R (V) G  I  N (I) F  T  R  L  Q  *
301 CGGTCAAGTG TTAATGACAT TGGTGATGAC TGGAAAGCTA CCAGGGTCGG CATCAACATC TTCACTCGCC TGCAGTGA
```

Figure 9

Monomeric avidin (clone M1)

```
  1 S  P  A  Q  P  A  M  A  R  K  C  S  L  T  G  K  W  T  N  D
  1 AGTCCGGCCC AGCCGGCCAT GGCGCGTAAA TGCAGCCTGA CCGGCAAATG GACCAACGAT
  1 TCAGGCCGGG TCGGCCGGTA CCGCGCATTT ACGTCGGACT GGCCGTTTAC CTGGTTGCTA
 21 L  G  S  N  M  T  I  G  A  V  N  S  R  G  E  F  T  G  I  Y
 61 CTGGGCTCCA ACATGACCAT CGGGGCTGTG AACAGCAGAG GTGAATTCAC AGGCACCTAC
 61 GACCCGAGGT TGTACTGGTA GCCCCGACAC TTGTCGTCTC CACTTAAGTG TCCGTGGATG
 41 I  T  A  V  T  A  T  S  N  E  I  K  E  S  P  L  H  G  T  Q
121 ATCACAGCCG TAACAGCCAC ATCAAATGAG ATCAAAGAGT CACCACTGCA TGGGACACAA
121 TAGTGTCGGC ATTGTCGGTG TAGTTTACTC TAGTTTCTCA GTGGTGACGT ACCCTGTGTT
 61 A  T  I  N  K  R  I  Q  P  T  F  G  F  T  V  A  W  K  F  S
181 GCCACCATCA ACAAGAGGAT CCAGCCCACC TTTGGCTTCA CCGTCGCTTG GAAGTTTTCA
181 CGGTGGTAGT TGTTCTCCTA GGTCGGGTGG AAACCGAAGT GGCAGCGAAC CTTCAAAAGT
 81 E  S  T  T  V  F  T  G  Q  C  F  I  D  R  N  G  L  *  K  L
241 GAGTCCACCA CTGTCTTCAC GGGCCAGTGC TTCATAGACA GGAATGGACT CTGAAAACTT
241 CTCAGGTGGT GACAGAAGTG CCCGGTCACG AAGTATCTGT CCTTACCTGA GACTTTTGAA
101 P  R  R  S  *  R  P  R  G  C  C  G  Q  V  L  M  T  L  V  M
301 CCAAGGAGGT CCTGAAGACC GGCGTGGCTG CTGCCGGTCA AGTGTTAATG ACATTGGTGA TG
301 GGTTCCTCCA GGACTTCTGG CCGCACCGAC GACGGCCAGT TCACAATTAC TGTAACCACT AC
121 T  G  K  L  P  G  P  A  P  T  S  S  L  A  C
361 ACTGGAAAGC TACCAGGGCC GGCGCCAACA TCTTCACTCG CCTGCAG
361 TGACCTTTCG ATGGTCCCGG CCGCGGTTGT AGAAGTGAGC GGACGTC
```

T - substitute by C  
Primer M1-F1  
5'-CAAGAGGACCCAGCCCACCTTTGGC-3'  
Primer M1-R2  
5'-TGGGCTGGGTCCTCTTGTTGATGGT-3'  
Primer M1-F3  
5'-AGGAATGGAAGGAGGTCCTGAAGA-3'  
Primer M1-R4  
5'-GGACCTCCTTCCCATTCCTGTCTAT-3'

Orientation

M13R  T3     5' Clone M1    3'
                              T7  M13F

— pCR4-TOPO vector

SEQ ID NO: 1 Chaperone protein dnaK (Heat shock protein 70) from
Mycobacterium tuberculosis (P0A5B9, GI:61222666)

```
  1  maravgidlg ttnsvvsvle ggdpvvvans egsrttpsiv afarngevlv gqpaknqavt
 61  nvdrtvrsvk rhmgsdwsie idgkkytape isarilmklk rdaeaylged itdavittpa
121  yfndaqrqat kdagqiagln vlrivnepta aalaygldkg ekeqrilvfd lgggtfdvsl
181  leigegvvev ratsgdnhlg gddwdqrvvd wlvdkfkgts gidltkdkma mqrlreaaek
241  akielsssqs tsinlpyitv dadknplfld eqltraefqr itqdlldrtr kpfqsviadt
301  gisvseidhv vlvggstrmp avtdlvkelt ggkepnkgvn pdevvavgaa lqagvlkgev
361  kdvllldvtp lslgietkgg vmtrliernt tiptkrsetf ttaddnqpsv qiqvyqgere
421  iaahnkllgs feltgippap rgipqievtf didangivhv takdkgtgke ntiriqegsg
481  lskedidrmi kdaeahaeed rkrreeadvr nqaetlvyqt ekfvkeqrea eggskvpedt
541  lnkvdaavae akaalggsdi saiksamekl gqesqalgqa iyeaaqaasq atgaahpgge
601  pggahpgsad dvvdaevvdd greak
```

SEQ ID NO: 2 Chaperone protein dnaK (Heat shock protein 70) from
Mycobacterium bovis (NP_854021.1 GI:31791528)

```
  1  maravgidlg ttnsvvsvle ggdpvvvans egsrttpsiv afarngevlv gqpaknqavt
 61  nvdrtvrsvk rhmgsdwsie idgkkytape isarilmklk rdaeaylged itdavittpa
121  yfndaqrqat kdagqiagln vlrivnepta aalaygldkg ekeqrilvfd lgggtfdvsl
181  leigegvvev ratsgdnhlg gddwdqrvvd wlvdkfkgts gidltkdkma mqrlreaaek
241  akielsssqs tsinlpyitv dadknplfld eqltraefqr itqdlldrtr kpfqsviadt
301  gisvseidhv vlvggstrmp avtdlvkelt ggkepnkgvn pdevvavgaa lqagvlkgev
361  kdvllldvtp lslgietkgg vmtrliernt tiptkrsetf ttaddnqpsv qiqvyqgere
421  iaahnkllgs feltgippap rgipqievtf didangivhv takdkgtgke ntiriqegsg
481  lskedidrmi kdaeahaeed rkrreeadvr nqaetlvyqt ekfvkeqrea eggskvpedt
541  lnkvdaavae akaalggsdi saiksamekl gqesqalgqa iyeaaqaasq atgaahpgge
601  pggahpgsad dvvdaevvdd greak
```

IMMUNOTHERAPIES EMPLOYING SELF-ASSEMBLING VACCINES

RELATED APPLICATIONS

This application is a 371 National Stage Application of PCT/US09/041029 filed on Apr. 17, 2009; which claims priority to U.S. Provisional Application Ser. No. 61/046,195, filed Apr. 18, 2008, the entire contents of which are expressly incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 16, 2011, is named MAA01801.txt and is 37,053 bytes in size.

BACKGROUND

Immunization with vaccines remains a cornerstone of protection against threat of disease and infection. The key difficulty in vaccine development is rapidly matching a vaccine, or antitoxin, to a specific threat. Current vaccine development strategies rely on the identification and characterization of antigens that can be targeted to successfully eradicate infection or disease. Current vaccine development strategies are time- and labor-intensive and can only commence once a threat emerges. Such strategies are also impractical for generating personalized vaccines to combat disease for which target antigens varies among individuals. Current vaccine development strategies are therefore insufficient if a new and serious threat were to emerge, for which sufficient time were not available to identify and characterize target antigens before such a threat could be contained. Current vaccine development strategies are also insufficient for generating personalized vaccines for the general population.

Thus, there is a need for a technology platform for generating personalized vaccines and to contain serious threats that quickly evolve, are fast-acting, and/or highly contagious.

SUMMARY OF THE INVENTION

In one aspect, the present invention features pharmaceutical compositions that can be administered to a subject to induce an immune response to an antigen of interest. In one embodiment, the compositions comprise a heat shock protein fused to a biotin-binding protein. In another embodiment, the compositions comprise a heat shock protein fused to a biotin-binding protein and non-covalently bound to at least one, two, three, or four biotinylated components. In certain embodiments, the biotinylated components are the same or different molecules. Non-limiting examples of biotinylated components include biotinylated proteins, cells, and viruses. Non-limiting examples of biotinylated proteins include biotinylated antigens, antibodies, and costimulatory molecules.

The compositions of the present invention can be used prophylactically to raise immunity against an antigen of interest, preventing the establishment and proliferation of viruses or cells in a subject expressing and exhibiting the antigen of interest or presenting portions thereof. In this manner, prevention of the establishment and proliferation of tumor or foreign cells expressing the antigen of interest may be achieved. The compositions provided herein can also be used therapeutically in a subject previously infected with viruses or harboring such cells to prevent further viral or cellular proliferation or to eliminate cells of the subject that proliferate, including tumor cells expressing and exhibiting the antigen of interest or presenting a portion of the antigen.

In another embodiment, compositions comprise expression vectors capable of directing the expression of heat shock protein fused to a biotin-binding protein and/or proteins to be biotinylated, as provided herein.

In yet a further embodiment, the present invention provides methods for producing a self-assembling pharmaceutical composition, comprising contacting a heat shock protein fused to a biotin-binding protein with four biotinylated components, sufficient to form a non-covalent complex of the heat shock protein and the four biotinylated components, wherein at least two of the four biotinylated components are not identical. The present invention also provides methods for inducing an immune response in a subject, comprising administering to the subject a heat shock protein fused to a biotin-binding protein and four biotinylated components, wherein at least two of the four biotinylated components are not identical. The present invention further provides methods for increasing the potency of a therapeutic in a subject, comprising administering to the subject a heat shock protein fused to a biotin-binding protein and four biotinylated components, wherein at least two of the four biotinylated components are not identical.

Administration of a biotinylated monoclonal antibody and a heat shock protein fused to a biotin-binding protein may dramatically boost the immune efficacy and potency of available monoclonal antibodies, which would otherwise serve as weak vaccine immunogens. Furthermore, the availability of a monoclonal antibody or an immune serum against a specific target antigen may alone be sufficient to produce an immunostimulatory complex that could stimulate the production of antibodies against an antigen of interest and the stimulation of cytotoxic T-cells. Finally, pharmaceutical compositions described herein would bypass the need to create scFv specific heat shock fusion proteins for each antigen specific scFv and or antibody.

Thus, the present invention provides distinct advantages over existing technologies in allowing for: 1) preparation of vaccine to unidentified, uncharacterized antigen or antigens; 2) preparation of personalized vaccines; 3) rapid production of pharmaceutical compositions (e.g., vaccines), which, in turn, allow for increased capacity for production of such of pharmaceutical compositions; and 4) "supercharging" existing therapeutics such as monoclonal antibodies. The technologies described herein provide for the self-assembly of fixed and potent adjuvants with a variety of different antigens, peptides, or antigen targeting molecules, including tumor antigen specific monoclonal antibodies of single-chain antibodies.

Further features and advantages will be described in the detailed description and claims.

BRIEF DESCRIPTION OF THE DRAWINGS

FIG. 1 illustrates modification of the pET-45b(+) expression vector. A) Schematic of the insertion of the SfiI restriction site. B) Final multiple cloning sites of the modified pET-45b(+) vector (SEQ ID NOS 6-7, respectively, in order of appearance).

FIG. 4 shows removal of NotI and SfiI sites by using PCR based site directed mutagenesis. Using modified primers containing the desired mutations, two overlapping PCR products were generated. These were extended by PCR in absence of primers followed by the addition of specific primers.

FIG. 5 shows introduction of the Ovalbumin peptide (residues 254-264) at the N-terminal of MTBhsp70. We designed a synthetic linker coding for the Ovalbumin peptide SIINFEKL (SEQ ID NO: 4)and digested it with SfiI and NotI. Similarly, we cut the pET-45b(+) MTBhsp70 plasmid with SfiI and NotI. Both components were ligated and the ligation product was used to transform competent bacteria. Ampicilin resistant colonies were picked and screened by sequencing.

FIG. 6 shows partial sequencing of the N-terminal region of $Ova_{257-264}$-MTBhsp70 (SEQ ID NO: 8).

FIG. 9 illustrates an amino acid and nucleotide comparison between wild-type (SEQ ID NOS 12 and 11, respectively, in order of appearance) and monomeric Avidin (SEQ ID NOS 10 and 9, respectively, in order of appearance).

FIG. 10 illustrates sequence errors corrected by PCR based mutagenesis. FIG. 10 discloses the coding nucleotide sequence as SEQ ID NO: 13, the coded amino acid sequences as SEQ ID NOS 13-16, respectively, in order of appearance, and the primer sequence as SEQ ID NOS 17-20, respectively, in order of appearance.

FIG. 11 discloses the "monomeric" sequence as SEQ ID NOS 22 and 21, respectively, in order of appearance, and the "wild-type" sequence as SEQ ID NOS 24 and 23, respectively, in order of appearance.

FIG. 14 depicts the full-length protein sequences of HSP70 from *Mycobacterium tuberculosis* HSP70 and *Mycobacterium bovus* HSP70, respectively.

DETAILED DESCRIPTION OF THE INVENTION

Definitions

For convenience, before further description of the present invention, certain terms employed in the specification, examples and appended claims are defined here.

The singular forms "a", "an", and "the" include plural references unless the context clearly dictates otherwise.

The term "administer" or "administering" includes any method of delivery of a pharmaceutical composition of the present invention, including systemic or localized administration. "Parenteral" means modes of administration other than enteral and topical administration, usually by injection, and includes, without limitation, intravenous, intramuscular, intralesional, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection, oral, epidural, intranasal, and infusion.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of the foregoing. The names of the natural amino acids are abbreviated herein in accordance with the recommendations of IUPAC-IUB.

The term "antibody" refers to an immunoglobulin, or derivatives thereof, which maintain specific binding ability, and proteins having a binding domain which is homologous or largely homologous to an immunoglobulin binding domain. The term "antibody" is intended to encompass whole antibodies or antigen-binding fragments thereof. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. An antibody may be an engineered or naturally occurring antibody.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', $F(ab')_2$, Fc, scFv, Fv, dsFv diabody, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

Figure 2:
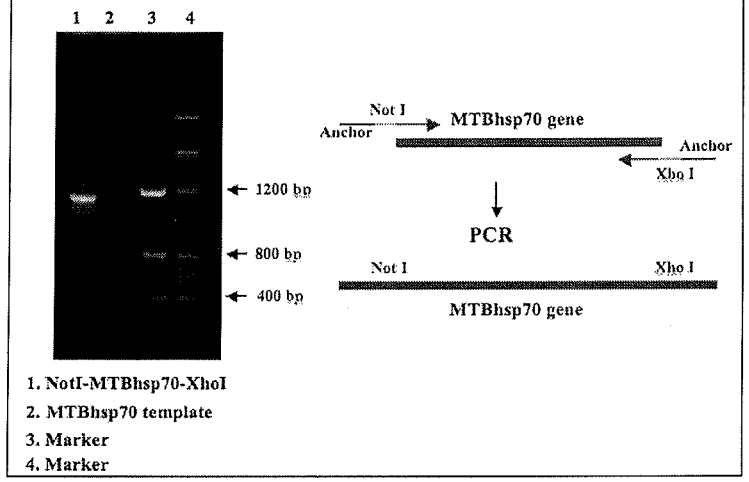
FIG. 2 shows introduction of NotI and XhoI restriction sites into MTBhsp70. Using primers overlapping the N- and C-terminals of MTBhsp70 a NotI site and an XhoI site were introduced by PCR. The resulting PCR product is shown in lane 1.

An "antigen" refers to a target of an immune response induced by a composition described herein. An antigen may be a protein antigen and is understood to include an entire protein, fragment of the protein exhibited on the surface of a virus or an infected, foreign, or tumor cell of a subject as well as peptide displayed by an infected, foreign, or tumor cell as a result of processing and presentation of the protein, for example, through the typical MHC class I or II pathways. Examples of such foreign cells include bacteria, fungi, and protozoa. Examples of bacterial antigens include Protein A (PrA), Protein G (PrG), and Protein L (PrL).

The term "antigen binding site" refers to a region of an antibody that specifically binds an epitope on an antigen.

The term "biotin-binding protein" refers to a protein, which non-covalently binds to biotin. A biotin-binding protein may be a monomer, dimer, or tetramer, capable of forming monovalent, divalent, or tetravalent pharmaceutical compositions, respectively, as described herein. Non-limiting examples include anti-biotin antibodies, avidin, streptavidin, and neutravidin. The avidin may comprise mature avidin, or a sequence that is at least 80%, 85%, 90%, 95%, or 99% identical to the sequence identified by NCBI Accession No. NP_990651. The streptavidin may comprise, for example, a sequence that is at least 80%, 85%, 90%, 95%, or 99% identical to the sequence identified by of NCBI Accession No. AAU48617. The term "biotin-binding protein" is intended to encompass wild-type and derivatives of avidin, streptavidin, and neutravidin, which form monomers, dimers or tetramers. Examples of such derivatives are set forth below and also described in Laitinen, O. H. (2007), "Brave New (Strept)avidins in Biotechnology," *Trends in Biotechnology* 25 (6): 269-277 and Nordlund, H. R. (2003), "Introduction of histidine residues into avidin subunit interfaces allows pH-dependent regulation of quaternary structure and biotin binding," *FEBS Letters* 555: 449-454, the contents of both of which are expressly incorporated herein by reference.

The term "cell" when used in the context as an antigen-containing biotinylated component is intended to encompass whole cells or portions thereof, provided that the portions contain the antigen of interest on a surface accessible for recognition by the immune system when a pharmaceutical composition comprising the biotinylated "cell" is administered to a subject.

The terms "comprise" and "comprising" are used in the inclusive, open sense, meaning that additional elements may be included.

The term "costimulatory molecule" as used herein includes any molecule which is able to either enhance the stimulating effect of an antigen-specific primary T cell stimulant or to raise its activity beyond the threshold level required for cellular activation, resulting in activation of naive T cells. Such a costimulatory molecule can be a membrane-resident receptor protein.

The term "effective amount" refers to that amount of a pharmaceutical composition which is sufficient to effect a desired result. An effective amount of a pharmaceutical composition can be administered in one or more administrations.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY). Examples of engineered antibodies include enhanced single chain monoclonal antibodies and enhanced monoclonal antibodies. Examples of engineered antibodies are further described in PCT/US2007/061554, the entire contents of which are incorporated herein by reference.

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" refers to a hybrid protein which comprises sequences from at least two different proteins. The sequences may be from proteins of the same or of different organisms. In various embodiments, the fusion protein may comprise one or more amino acid sequences linked to a first protein. In the case where more than one amino acid sequence is fused to a first protein, the fusion sequences may be multiple copies of the same sequence, or alternatively, may be different amino acid sequences. A first protein may be fused to the N-terminus, the C-terminus, or the N- and C-terminus of a second protein.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')$_2$ fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain. "Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

"Host cell" refers to a cell that may be transduced with a specified transfer vector. The cell is optionally selected from in vitro cells such as those derived from cell culture, ex vivo cells, such as those derived from an organism, and in vivo cells, such as those in an organism. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "immunogenic" refers to the ability of a substance to elicit an immune response. An "immunogenic composition," or "immunogen" is a composition or substance which elicits an immune response. An "immune response" refers to the reaction of a subject to the presence of an antigen, which may include at least one of the following: making antibodies, developing immunity, developing hypersensitivity to the antigen, and developing tolerance.

The term "including" is used herein to mean "including but not limited to". "Including" and "including but not limited to" are used interchangeably.

A "linker" is art-recognized and refers to a molecule or group of molecules connecting two covalent moieties, such as a heat shock protein and biotin-binding protein. The linker may be comprised of a single linking molecule or may comprise a linking molecule and a spacer molecule, intended to separate the linking molecule and a moiety by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "multivalent" when in reference to a self-assembling pharmaceutical composition described herein refers to a heat shock fusion protein that is non-covalently bound to more than one biotinylated component. The term "divalent" when in reference to a self-assembling pharmaceutical composition described herein refers to a heat shock fusion protein that is non-covalently bound to two biotinylated components. The term "tetravalent" when in reference to a self-assembling pharmaceutical composition described herein refers to a heat shock fusion protein that is non-covalently bound to four biotinylated components. The biotinylated components of a multivalent pharmaceutical composition may have identical or different identities.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

A "patient" or "subject" or "host" are used interchangeably, and each refers to either a human or non-human animal.

The phrase "pharmaceutically acceptable" is employed herein to refer to those pharmaceutical compositions which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable carrier" as used herein means a pharmaceutically-acceptable material, composition or vehicle, such as a liquid or solid filler, diluent, excipient, or solvent encapsulating material, involved in carrying or transporting the subject pharmaceutical composition from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Unless the context clearly indicates otherwise, "protein," "polypeptide," and "peptide" are used interchangeably herein when referring to a gene expression product, e.g., an amino acid sequence as encoded by a coding sequence. A "protein" may also refer to an association of one or more proteins, such as an antibody. A "protein" may also refer to a protein fragment. A protein may be a post-translationally modified protein such as a glycosylated protein. By "gene expression product" is meant a molecule that is produced as a result of transcription of an entire or part of a gene. Gene products include RNA molecules transcribed from a gene, as well as proteins translated from such transcripts. Proteins may be naturally occurring isolated proteins or may be the product of recombinant or chemical synthesis. The term "protein fragment" refers to a protein in which amino acid residues are deleted as compared to the reference protein itself, but where the remaining amino acid sequence is usually identical to that of the reference protein. Such deletions may occur at the amino-terminus or carboxy-terminus of the reference protein, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. Fragments of may be obtained using proteinases to fragment a larger protein, or by recombinant methods, such as the expression of only part of a protein-encoding nucleotide sequence (either alone or fused with another protein-encoding nucleic acid sequence). In various embodiments, a fragment may comprise an enzymatic activity and/or an interaction site of the reference protein to, e.g., a cell receptor. In another embodiment, a fragment may have immunogenic properties. The proteins may include mutations introduced at particular loci by a variety of known techniques, which do not adversely effect, but may enhance, their use in the methods provided herein. A fragment can retain one or more of the biological activities of the reference protein.

The term "self-assembling" as used herein refers to the ability of a heat shock protein fused to a biotin-binding protein to form a non-covalent complex with biotinylated component(s) as described herein. Such ability is conferred by the non-covalent association of biotin with a biotin-binding protein.

The term "single chain variable fragment" or "scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

"Treating" a disease in a subject or "treating" a subject having a disease refers to subjecting the subject to a pharmaceutical treatment, e.g., the administration of a drug, such that the extent of the disease is decreased or prevented. Treatment includes (but is not limited to) administration of a composition, such as a pharmaceutical composition, and may be performed either prophylactically, or subsequent to the initiation of a pathologic event.

The term "vaccine" refers to a pharmaceutical composition that elicits an immune response to an antigen of interest. The vaccine may also confer protective immunity upon a subject.

"Vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops, which, in their vector form are not bound to the chromosome. In the present specification, "plasmid" and "vector" are used interchangeably as the plasmid is the most commonly used form of vector. However, as will be appreciated by those skilled in the art, the invention is intended to include such other forms of expression vectors which serve equivalent functions and which become subsequently known in the art.

The term "virus" when used in the context as an antigen-containing biotinylated component is intended to encompass whole viral particles or portions thereof, provided that the portions contain the antigen of interest on a surface accessible for recognition by the immune system when a pharmaceutical composition comprising the biotinylated "virus" is administered to a subject.

General

Featured herein is a novel vaccine platform that combines multiple immunologic components to generate a highly potent immune response when administered to a subject. Compositions and methods of linking the multiple subunits for rapid assembly of the new vaccine are also provided.

The present invention is based at least in part on the discovery that a heat shock protein fusion in non-covalent association with a biotinylated component of antibody or antigen results in a composition that strongly stimulates cellular, in particular cell-mediated cytolytic, responses against the non-covalently associated protein antigen, which responses can kill cells exhibiting the antigen.

Heat Shock Protein Fusions

A "heat shock protein" is encoded by a "heat shock gene" or a stress gene, and refers a gene that is activated or otherwise detectably upregulated due to the contact or exposure of an organism (containing the gene) to a stressor, such as heat shock, hypoxia, glucose deprivation, heavy metal salts, inhibitors of energy metabolism and electron transport, and protein denaturants, or to certain benzoquinone ansamycins. Nover, L., Heat Shock Response, CRC Press, Inc., Boca Raton, Fla. (1991). "Heat shock protein" also includes homologous proteins encoded by genes within known stress gene families, even though such homologous genes are not themselves induced by a stressor.

A "heat shock protein fusion" refers to a heat shock protein linked to a biotin-binding protein. For example, a heat shock protein may be C- or N-terminally joined to a biotin-binding protein to generate a heat shock protein fusion. When administered in conjunction with a biotinylated component provided herein, a heat shock protein fusion is capable of stimulating or enhancing humoral and/or cellular immune responses, including CD8 cytotoxic T cell (CTL) responses, to an antigen of interest.

For example, but not by way of limitation, heat shock proteins which may be used according to the invention include BiP (also referred to as grp78), Hsp10, Hsp20-30, Hsp60 hsp70, hsc70, gp96 (grp94), hsp60, hsp40, and Hsp100-200, Hsp100, Hsp90, and members of the families thereof. Especially preferred heat shock proteins are BiP, gp96, and hsp70, as exemplified below. A particular group of heat shock proteins includes Hsp90, Hsp70, Hsp60, Hsp20-30, further preferably Hsp70 and Hsp60. Most preferred is a member of the hsp70 family.

Hsp10 examples include GroES and Cpn10. Hsp10 is typically found in *E. coli* and in mitochondria and chloroplasts of eukaryotic cells. Hsp10 forms a seven-membered ring that associates with Hsp60 oligomers. Hsp10 is also involved in protein folding.

Hsp60 examples include Hsp65 from mycobacteria. Bacterial Hsp60 is also commonly known as GroEL, such as the GroEL from *E. coli*. Hsp60 forms large homooligomeric complexes, and appears to play a key role in protein folding. Hsp60 homologues are present in eukaryotic mitochondria and chloroplasts.

Hsp70 examples include Hsp72 and Hsc73 from mammalian cells, DnaK from bacteria, particularly mycobacteria such as *Mycobacterium leprae*, *Mycobacterium tuberculosis* (MTb), and *Mycobacterium bovis* (such as Bacille-Calmette Guerin; referred to herein as Hsp71), DnaK from *Escherichia coli*, yeast, and other prokaryotes, and BiP and Grp78. Hsp70 is capable of specifically binding ATP as well as unfolded proteins, thereby participating in protein folding and unfolding as well as in the assembly and disassembly of protein complexes. In a preferred embodiment, the heat shock protein is or is derived from MTb HSP 70. The full-length protein sequences of *Mycobacterium tuberculosis* HSP70 and *Mycobacterium bovis* HSP70 are depicted in FIG. 2 as SEQ ID NOs: 1 and 2, respectively. A heat shock protein fusion to be used in conjunction with the methods described herein may comprise a sequence that is at least 80%, 85%, 90%, 95%, or 99% identical to SEQ ID NO: 1 or 2.

Hsp90 examples include HtpG in *E. coli*, Hsp83 and Hsc83 yeast, and Hsp90 alpha, Hsp90 beta and Grp94 in humans. Hsp90 binds groups of proteins, which proteins are typically cellular regulatory molecules such as steroid hormone receptors (eg., glucocorticoid, estrogen, progesterone, and testosterone receptors), transcription factors and protein kinases that play a role in signal transduction mechanisms. Hsp90 proteins also participate in the formation of large, abundant protein complexes that include other heat shock proteins.

Hsp100 examples include mammalian Hsp 110, yeast Hsp104, ClpA, ClpB, ClpC, ClpX and ClpY. Yeast Hsp104 and *E. coli* ClpA, form hexameric and *E. coli* ClpB, tetrameric particles whose assembly appears to require adenine nucleotide binding. Clp protease provides a 750 kDa heterooligomer composed of ClpP (a proteolytic subunit) and of ClpA. ClpB-Y are structurally related to ClpA, although unlike ClpA they do not appear to complex with ClpP.

Hsp100-200 examples include Grp170 (for glucose-regulated protein). Grp170 resides in the lumen of the ER, in the pre-golgi compartment, and may play a role in immunoglobulin folding and assembly.

Naturally occurring or recombinantly derived mutants of heat shock proteins may be used according to the invention. For example, but not by way of limitation, the present invention provides for the use of heat shock proteins mutated so as to facilitate their secretion from the cell (for example having mutation or deletion of an element which facilitates endoplasmic reticulum recapture, such as KDEL (SEQ ID NO:3) or its homologues; such mutants are described in PCT Application No. PCT/US96/13233 (WO 97/06685), which is incorporated herein by reference).

In particular embodiments, the heat shock proteins of the present invention are obtained from enterobacteria, mycobacteria (particularly M. leprae, M. tuberculosis, M. vaccae, M. smegmatis and M. bovis), E. coli, yeast, Drosophila, vertebrates, avians, chickens, mammals, rats, mice, primates, or humans.

The pharmaceutical compositions provided herein may have individual amino acid residues that are modified by oxidation or reduction. Furthermore, various substitutions, deletions, or additions may be made to the amino acid or nucleic acid sequences, the net effect of which is to retain or further enhance the increased biological activity of the heat shock protein. Due to code degeneracy, for example, there may be considerable variation in nucleotide sequences encoding the same amino acid sequence. The term "heat shock protein" is intended to encompass fragments of heat shock proteins obtained from heat shock proteins, provided such fragments include the epitopes involved with enhancing the immune response to an antigen of interest. Fragments of heat shock proteins may be obtained using proteinases, or by recombinant methods, such as the expression of only part of a stress protein-encoding nucleotide sequence (either alone or fused with another protein-encoding nucleic acid sequence). The heat shock proteins may include mutations introduced at particular loci by a variety of known techniques to enhance its effect on the immune system. See, e.g., Sambrook et al., Molecular Cloning: A Laboratory Manual, 2d Ed., Cold Spring Harbor Laboratory Press (1989); Drinkwater and Klinedinst Proc. Natl. Acad. Sci. USA 83:3402-3406 (1986); Liao and Wise, Gene 88:107-111 (1990); Horwitz et al., Genome 3:112-117 (1989).

In particular embodiments, e.g., in heat shock protein fusions involving chemical conjugates between a heat shock protein and a biotin-binding protein, the heat shock proteins used in the present invention are isolated heat shock proteins, which means that the heat shock proteins have been selected and separated from the host cell in which they were produced. In some embodiments where the heat shock is expressed recombinantly as a fusion of a heat shock protein fused to a biotin-binding protein, the heat shock protein fusions used in the present invention are isolated heat shock protein fusions, which means that the heat shock protein fusions have been selected and separated from the host cell in which they were produced. Such isolation can be carried out as described herein and using routine methods of protein isolation known in the art. Maniatis et al., Molecular Cloning, A Laboratory Manual, Cold Spring Harbor Laboratory, Cold Spring Harbor, N.Y. (1982); Sambrook et al., Molecular Cloning: A Laboratory Manual, 2d Ed., Cold Spring Harbor Laboratory Press (1989); Deutscher, M., Guide to Protein Purification Methods Enzymology, vol. 182, Academic Press, Inc., San Diego, Calif. (1990).

Biotinylated Components

The term "biotinylated component" as used herein, refers to a biotinylated protein, cell, or virus. Non-limiting examples of biotinylated proteins include biotinylated antigens, antibodies, and costimulatory molecules. The biotinylated component is to be administered to a subject in conjunction with a heat shock protein fusion as described herein.

i) Antigen-Containing Biotinylated Components

In one embodiment, the biotinylated component is derived from a subject, which may be the same or a different person to whom the pharmaceutical compositions are to be administered. For example, a protein, cell, and/or virus to which an immune response is desired can be isolated from a subject and optionally be amplified or cloned in vitro. The protein, cell, and/or virus may then be biotinylated in vitro using methods known in the art. The biotinylated component may then be administered in conjunction with a heat shock protein fusion described herein to the identical subject from which the protein, cell, and/or virus was isolated, thus allowing for the development of personalized vaccines. Alternatively, the biotinylated component may be administered in conjunction with a heat shock protein fusion described herein to a different subject from which the protein, cell, and/or virus was isolated. The latter approach allows for the development of vaccines for the general population against a disease or infectious agent when administered to a general population.

Both approaches provide distinct advantages over the art, namely that, the component need only be identified to the extent that allows for its correlation to a specific disease or infection and allows for its isolation from the subject. Such is a novel approach for targeting antigens whose sequence may not be known or structure even identified. Thus, the present invention allows for the preparation of pharmaceutical compositions to induce an immune response to known or unidentified, uncharacterized antigen or antigens. Personalized vaccines provide an additional advantage over conventional vaccines in that HLA restriction is not problematic because the cell or protein such as an antibody for example, is derived from the identical host that the biotinylated component is to be administered.

In place of directly linking synthetic antigen peptides to heat shock proteins to generate a vaccine, scFVs, for example, may instead be conjugated to biotin and administered in conjunction with a heat shock protein fusion moiety described herein, thus employing a novel fusion protein vaccine for presenting antigen to APCs in order to generate both a humoral and CD-8 response. The scFV1s can, for example, be selected for by their binding to an uncharacterized antigen or to a characterized antigen by binding studies. In this example, the scFVs are to be biotinylated and administered in conjunction with a heat shock protein fusion moiety, for example.

In much the same way, any protein, cell, and/or virus may be biotinylated and administered to a subject in conjunction with a heat shock protein fusion moiety described herein, such that the biotinylated protein, cell, and/or virus when administered in conjunction with a heat shock fusion protein described herein targets an immune response to an antigen of interest.

An example of such a cell is a tumor cell isolated from a subject, which is biotinylated and administered in conjunction with a heat shock protein fusion described herein. The tumor cell prior to introduction or reintroduction into a subject in the present invention is to be treated such that the cell no longer reproduces and causes harm to the subject to which it is administered. Such may be achieved by sublethally irradiating the tumor cell before or after biotinylation. The tumor cell expresses antigen on its surface, the identity of which may or may not be known or characterized. When administered to a subject in conjunction with the heat shock protein fusion, the non-covalent complex induces an immune response to the tumor antigen. The result is a "killer T cell" response against the cell expressing antigen, thereby targeting the diseased cell types for destruction.

The tumor cell is a cell of a type of cancer to be treated or prevented by the methods of the present invention. Such cells include, but are not limited to, for example, a human sarcoma cell or carcinoma cell, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, or heavy chain disease cell.

Other cells that may be biotinylated and administered in conjunction with a heat shock protein fusion in the same fashion as described above include any cells in a subject to which a "killer T cell" response is desired. Examples of such cells include other diseased and/or virally infected cells expressing antigen on their surface. As described above for tumor cells, these cells prior to introduction or reintroduction into a subject in the present invention are preferably treated such that the cells no longer reproduce or cause harm to the subject. Such may be achieved by sublethally irradiating the cells before or after biotinylation. Such cells may be treated so that they are rendered non-infectious or, if a toxin-secreting cell, no longer secrete toxin.

Infectious diseases that can be treated or prevented by the methods of the present invention are caused by infectious agents. Such infectious agents or antigens derived therefrom, that may be biotinylated and administered in conjunction with the present invention, include, but are not limited to, viruses, bacteria, fungi, and protozoa. The invention is not limited to treating or preventing infectious diseases caused by intracellular pathogens but is intended to include extracellular pathogens as well. Many medically relevant microorganisms have been described extensively in the literature, e.g., see C. G. A Thomas, Medical Microbiology, Bailliere Tindall, Great Britain 1983, the entire contents of which is hereby incorporated by reference.

In one embodiment, virus expressing antigen or viral antigen may be biotinylated and administered in conjunction with a heat shock protein fusion in the same fashion as described above.

Infectious viruses of both human and non-human vertebrates, include retroviruses, RNA viruses and DNA viruses expressing antigen. Examples of viruses include but are not limited to: Retroviridae (e.g. human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e. Hepatitis C); Norwalk and related viruses, and astroviruses).

Retroviruses that are contemplated include both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of RNA viruses that are antigens in vertebrate animals include, but are not limited to, the following: members of the family Reoviridae, including the genus *Orthoreovirus* (multiple serotypes of both mammalian and avian retroviruses), the genus *Orbivirus* (Bluetongue virus, Eugenangee virus, Kemerovo virus, African horse sickness virus, and Colorado Tick Fever virus), the genus *Rotavirus*

(human rotavirus, Nebraska calf diarrhea virus, murine rotavirus, simian rotavirus, bovine or ovine rotavirus, avian rotavirus); the family Picomaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, Poliovirus muris, Bovine enteroviruses, Porcine enteroviruses, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, Feline picornavirus and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza virus* (Influenza virus type A, many human subtypes); Swine influenza virus, and Avian and Equine Influenza viruses; influenza type B (many human subtypes), and influenza type C (possible separate genus); the family *paramyxoviridae*, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); forest virus, Sindbis virus, Chikungunya virus, O'Nyong-Nyong virus, Ross river virus, Venezuelan equine encephalitis virus, Western equine encephalitis virus), the genus *Flavirius* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus *Pestivirus* (Mucosal disease virus, Hog cholera virus, Border disease virus); the family Bunyaviridae, including the genus *Bunyvirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *Influenza* virus (Influenza virus type A, many human subtypes); Swine influenza virus, and Avian and Equine Influenza viruses; influenza type B (many human subtypes), and influenza type C (possible separate genus); the family paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), ChanBipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Mouse Hepatitis virus, Human enteric corona virus, and Feline infectious peritonitis (Feline coronavirus).

Illustrative DNA viruses that are antigens in vertebrate animals include, but are not limited to: the family Poxyiridae, including the genus *Orthopoxvirus* (Variola major, Variola minor, Monkey pox Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A, B, C, D, E and ungrouped; simian adenoviruses (at least 23 serotypes), infectious canine hepatitis, and adenoviruses of cattle, pigs, sheep, frogs and many other species, the genus *Aviadenovirus* (Avian adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus *Adeno*-associated viruses, the genus *Parvovirus* (Feline panleukopenia virus, bovine parvovirus, canine parvovirus, Aleutian mink disease virus, etc). Finally, DNA viruses may include viruses which do not fit into the above families such as Kuru and Creutzfeldt-Jacob disease viruses and chronic infectious neuropathic agents.

ii) Antibody-Containing Biotinylated Components

In another embodiment, immunotherapeutic agents, such as antibodies may be biotinylated and administered in conjunction with a heat shock protein fusion as described herein. Natural antibodies are themselves dimers, and thus, bivalent. If two hybridoma cells producing different antibodies are artificially fused, some of the antibodies produced by the hybrid hybridoma are composed of two monomers with different specificities. Such bispecific antibodies can also be produced by chemically conjugating two antibodies. Natural antibodies and their bispecific derivatives are relatively large and expensive to produce. The constant domains of mouse antibodies are also a major cause of the human anti-mouse antibody (HAMA) response, which prevents their extensive use as therapeutic agents. They can also give rise to unwanted effects due to their binding of Fc-receptors. For these reasons, molecular immunologists have been concentrating on the production of the much smaller Fab- and Fv-fragments in microorganisms. These smaller fragments are not only much easier to produce, they are also less immunogenic, have no effector functions, and, because of their relatively small size, they are better able to penetrate tissues and tumors. In the case of the Fab-fragments, the constant domains adjacent to the variable domains play a major role in stabilizing the heavy and light chain dimer. Accordingly, while antibodies to be used in conjunction with the present methods may include full-length or nearly full length engineered antibodies, smaller, single domain engineered antibodies (that may be multivalent and multispecific) may be preferred.

The Fv-fragment is much less stable, and a peptide linker may therefore be introduced between the heavy and light chain variable domains to increase stability. This construct is known as a single chain Fv(scFv)-fragment. A disulfide bond is sometimes introduced between the two domains for extra stability.

Bivalent and bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular $V_H$-$V_L$ pairings with formation of a 60 kDa non-covalent scFv dimer "diabody" (Holliger et al., 1993, Proc. Natl. Acad. Sci. USA 90, 6444-6448). The diabody format can also be used for generation of recombinant bispecific antibodies, which are obtained by the noncovalent association of two single-chain fusion products, consisting of the $V_H$ domain from one antibody connected by a short linker to the $V_L$ domain of another antibody. Reducing the linker length still further below three residues can result in the formation of trimers ("triabody", about 90 kDa) or tetramers ("tetrabody", about 120 kDa) (Le Gall et al., 1999, FEBS Letters 453, 164-168). For a review of engineered antibodies, particularly single domain fragments, see Holliger and Hudson, 2005, Nature Biotechnology, 23:1126-1136. All of such engineered antibodies may be conjugated to biotin and used in the methods provided herein.

Other multivalent engineered antibodies that may be used in conjunction with the present embodiments are described in Lu, et al., 2003, J. Immunol. Meth. 279:219-232 (di-diabodies or tetravalent bispecific antibodies); US Published Application 20050079170 (multimeric Fv molecules or "flexibodies"), and WO99/57150 and Kipriyanov, et al., 1999, J. Mol. Biol. 293:41-56 (tandem diabodies, or "Tandabs").

Any of the above-described multivalent engineered antibodies may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559); Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; Beidler et al. (1988) J. Immunol. 141:4053-4060; and Winter and Milstein, Nature, 349, pp. 293-99 (1991)). Preferably non-human antibodies are "humanized" by linking the non-human antigen binding domain with a human constant domain (e.g. Cabilly et al., U.S. Pat. No. 4,816,567; Morrison et al., Proc. Natl. Acad. Sci. U.S.A., 81, pp. 6851-55 (1984)).

The antigen recognition sites or entire variable regions of the engineered antibodies may be derived from one or more parental antibodies directed against any antigen of interest. The parental antibodies can include naturally occurring antibodies, antibodies adapted from naturally occurring antibodies, or antibodies constructed de novo using sequences of antibodies or known to be specific for an antigen of interest. Sequences that may be derived from parental antibodies include heavy and/or light chain variable regions and/or CDRs, framework regions or other portions thereof.

Multivalent, multispecific antibodies may contain a heavy chain comprising two or more variable regions and/or a light chain comprising one or more variable regions wherein at least two of the variable regions recognize different epitopes on the same antigen.

Candidate antibodies to be biotinylated, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In one embodiment, the antibodies are monoclonal antibodies and/or have in vivo therapeutic and/or prophylactic uses against cancer. In some embodiments, the antibodies can be used for treatment and/or prevention of infectious disease. Examples of therapeutic and prophylactic antibodies include, but are not limited to, ERBITUX® (Cetuximab) (ImClone System), MDX-010 (Medarex, N.J.) which is a humanized anti-CTLA-4 antibody currently in clinic for the treatment of prostate cancer; SYNAGIS® (MedImmune, Md.) which is a humanized anti-respiratory syncytial virus (RSV) monoclonal antibody for the treatment of patients with RSV infection; HERCEPTIN® (Trastuzumab) (Genentech, Calif.) which is a humanized anti-HER2 monoclonal antibody for the treatment of patients with metastatic breast cancer. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IGGI antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM 3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD 40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tan-ox Biosystems); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β2-integrin IgG antibody (LeukoSite); Anti-LFA-1 is a murine anti CD18 F(ab')$_2$ (Pasteur-Merieux/Immunotech-); CAT-152 is a human anti-TGF-β2 antibody (Cambridge Ab Tech); and Corsevin M is a chimeric anti-Factor VII antibody (Centocor).

Self-Assembling Vaccines

Multiple biotinylated components may be administered in conjunction with a heat shock protein fusion as further described. In this way, multivalent pharmaceutical compositions may be generated and administered to a subject. The generation of multivalent pharmaceutical compositions allow for the production of "supercharged," or more potent vaccines and therapeutics. When the biotinylated component comprises an antibody, such vaccine exhibits activity improvement for marketed antibodies.

Wherein the pharmaceutical composition is multivalent, the biotinylated components to be administered may be any combination of biotinylated components described herein. For example, biotinylated components of the same or different identities may be administered in conjunction with a heat shock protein fusion as provided herein, provided that the biotin-binding protein, and in turn the heat shock protein fusion, is multivalent, or capable of binding multiple biotinylated components. As an example, the wild-type biotin-binding protein avidin has four biotin-binding sites and is therefore capable of binding four biotinylated components. In this example, the four sites are to be bound by four biotinylated components, and the biotin-binding components may be mixed and matched based on identity in any possible permutation of one, two, three, or four identical biotinylated components described herein. Four identical biotinylated components may be bound to the four biotin-binding sites.

Therefore, an effective amount of a biotinylated component with a first identity may be may be administered to a subject in conjunction with a heat shock protein fused to a biotin-binding protein, sufficient to form a pharmaceutical composition comprising four parts biotinylated component of a first identity and one part heat shock protein fused to a biotin-binding protein. Alternatively, an effective amount of biotinylated components with a first and second identity may be may be administered to a subject in conjunction with a heat shock protein fused to a biotin-binding protein, sufficient to form a pharmaceutical composition comprising three parts biotinylated component of a first identity, one part biotinylated component of a second identity, and one part heat shock protein fusion. In another embodiment, an effective amount of biotinylated components with a first and second identity may be administered to a subject in conjunction with a heat shock protein fused to a biotin-binding protein, sufficient to form a pharmaceutical composition comprising two parts biotinylated component of a first identity, two parts biotinylated component of a second identity, and one part heat shock protein fusion.

Wherein the self-assembling pharmaceutical composition is divalent, an effective amount of biotinylated component of a first identity be may be administered to a subject in conjunction with a heat shock protein fused to a biotin-binding protein, sufficient to form a pharmaceutical composition comprising two parts biotinylated component of a first identity and one part heat shock protein fusion. Alternatively, an effective amount of biotinylated components with a first and second identity may be may be administered to a subject in conjunction with a heat shock protein fused to a biotin-binding protein, sufficient to form a pharmaceutical composition comprising one part biotinylated component of a first identity, one part biotinylated component of a second identity, and one part heat shock protein fusion.

A biotinylated component of a multivalent pharmaceutical composition may include a costimulatory molecule, or a blocking group (i.e., biotin alone or biotin conjugated to a non-functional molecule). Examples of costimulatory molecules that may be administered in conjunction with the present invention include B7 molecules, including B7-1 (CD80) and B7-2 (CD86), CD28, CD58, LFA-3, CD40, B7-H3, CD137 (4-1BB), and interleukins (e.g., IL-1, IL-2, or IL-12). As an example, one part biotinylated component comprising a costimulatory molecule may be administered in conjunction with i) three parts of another biotinylated component comprising a protein, cell or virus; and ii) one part heat shock protein fused to a biotin-binding protein. In another example, two parts biotinylated component comprising a costimulatory molecule may be administered in conjunction with i) two parts of another biotinylated component comprising a protein, cell, or virus; and ii) one part heat shock protein fused to a biotin-binding protein. In another example, three parts biotinylated component comprising a costimulatory molecule may be administered in conjunction with i) one part of another biotinylated component comprising a protein, cell, or virus; and ii) one part heat shock protein fused to a biotin-binding protein.

A pH-sensitive mutant of avidin, streptavidin, or neutravidin, for example, may be employed to control the noncovalent interaction of avidin-, streptavidin-, or neutravidin- to biotin, and thereby achieve the desired stoichiometry of heat shock protein fusion with the various permutations and combinations of biotinylated component, as described herein. The choice of wild-type or a particular mutant form of biotin-binding protein such as avidin may be employed to control the desired valency of the pharmaceutical composition (e.g., monomeric, dimeric, or tetrameric form of avidin). Monovalent or divalent vaccines may be similarly produced by employing heat shock fusion proteins comprising other avidin, streptavidin, or neutravidin mutant proteins that bind biotin but in a monovalent or divalent fashion. An example of an avidin mutant is described in the Exemplification section below. An example of a pH-sensitive point mutant of Avidin which confers pH-adjustable biotin binding is Y33H. Another mutant has substitutions of histidine for Met96, Val115, and Ile117, optionally with histidine replacement at Trp110. Such approaches for controlling biotin-streptavidin binding are described in Laitinen, O. H. (2007), "Brave New (Strept)avidins in Biotechnology," *Trends in Biotechnology* 25 (6): 269-277 and Nordlund, H. R. (2003), "Introduction of histidine residues into avidin subunit interfaces allows pH-dependent regulation of quaternary structure and biotin binding," *FEBS Letters* 555: 449-454, the contents of both of which are incorporated herein by reference.

Methods of Producing the Self-Assembling Pharmaceutical Compositions

In one embodiment of the present invention, compositions are comprised of two moieties: a heat shock protein fused to a biotin-binding protein and a biotinylated component which targets the immune response to the antigen to which the immune response is desired. The present invention provides for fast, easy production of large amounts pharmaceutical composition (e.g., vaccine) because the production of biotinylated antigens or antibodies is well known and rapid, which, in turn, allows for an increased capacity for vaccine production. Because a heat shock protein fusion of a single identity may be administered in conjunction with any of a number of various biotinylated components as described herein, the heat shock fusion protein need not be synthesized de novo each time a new target antigen of interest is identified. Therefore, such methods of production are particularly rapid once the heat shock protein fusion to be administered is established and has been produced.

Provided are methods for making the heat shock protein fused to a biotin-binding protein. The heat shock protein may be prepared, using standard techniques, from natural sources, for example as described in Flynn et al., Science 245:385-390 (1989), or using recombinant techniques such as expression of a heat shock encoding gene construct in a suitable host cell such as a bacterial, yeast or mammalian cell. A fusion protein including the heat shock protein and biotin-binding protein can be produced by recombinant means. For example, a nucleic acid encoding the heat shock protein can be joined to either end of a nucleic acid sequence encoding the biotin-binding protein such that the two protein-coding sequences are sharing a common translational reading frame and can be expressed as a fusion protein including the biotin-binding protein and the heat shock protein. The combined sequence is inserted into a suitable vector chosen based on the expression features desired and the nature of the host cell. In the examples provided hereinafter, the nucleic acid sequences are assembled in a vector suitable for protein expression in the bacterium *E. coli*. Following expression in the chosen host cell, the fusion protein can be purified by routine biochemical separation techniques or by immunoaffinity methods using an antibody to one or the other part of the fusion protein. Alternatively, the selected vector can add a tag to the fusion protein sequence, e.g., an oligohistidine tag as described in the examples presented hereinafter, permitting expression of a tagged fusion protein that can be purified by affinity methods using an antibody or other material having an appropriately high affinity for the tag. Sambrook et al., Molecular Cloning: A Laboratory Manual, 2d Ed., Cold Spring Harbor Laboratory Press (1989); Deutscher, M. Guide to Protein Purification Methods Enzymology, vol. 182. Academic Press, Inc. San Diego, Calif. (1990). If a vector suitable for expression in mammalian cells is used. e.g., one of the vectors discussed below, the heat shock protein fusion can be expressed and purified from mammalian cells. Alternatively, the mammalian expression vector (including fusion protein-coding sequences) can be administered to a subject to direct expression of heat shock protein fusion protein in the subject's cells. A nucleic acid encoding a heat shock protein can also be produced chemically and then inserted into a suitable vector for fusion protein production and purification or administration to a subject. Finally, a fusion protein can also be prepared chemically.

Techniques for making fusion genes are well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992). Accordingly, provided is an isolated nucleic acid comprising a fusion gene of a gene encoding a heat shock protein fused to a gene encoding a biotin-binding protein.

The nucleic acid may be provided in a vector comprising a nucleotide sequence encoding the heat shock protein fusion, and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered. Such vectors may be administered in any biologically effective carrier, e.g., any formulation or composition capable of effectively transfecting cells either ex vivo or in vivo with genetic material encoding a chimeric polypeptide. Approaches include insertion of the nucleic acid in viral vectors including recombinant retroviruses, adenoviruses, adeno-associated viruses, human immunodeficiency viruses, and herpes simplex viruses-1, or recombinant bacterial or eukaryotic plasmids. Viral vectors may be used to transfect cells directly; plasmid DNA may be delivered alone with the help of, for example, cationic liposomes (lipofectin) or derivatized (e.g., antibody conjugated), polylysine conjugates, gramicidin S, artificial viral envelopes or other such intracellular carriers. Nucleic acids may also be directly injected. Alternatively, calcium phosphate precipitation may be carried out to facilitate entry of a nucleic acid into a cell.

The subject nucleic acids may be used to cause expression and over-expression of a heat shock protein fusion protein in cells propagated in culture, e.g. to produce fusion proteins.

Provided also is a host cell transfected with a recombinant gene in order to express the heat shock protein fusion. The host cell may be any prokaryotic or eukaryotic cell. For example, a heat shock protein fusion may be expressed in bacterial cells, such as *E. coli*, insect cells (baculovirus), yeast, insect, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the fusion polypeptide will be known to those in the art.

A cell culture includes host cells, media and other byproducts. Suitable media for cell culture are well known in the art. A fusion polypeptide may be secreted and isolated from a mixture of cells and medium comprising the polypeptide. Alternatively, a fusion polypeptide may be retained cytoplasmically and the cells harvested, lysed and the protein isolated. A fusion polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a fusion.

Thus, a nucleotide sequence encoding all or part of the heat shock protein fusion may be used to produce a recombinant form of a protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant fusion polypeptides by microbial means or tissue-culture technology in accord with the subject invention.

Expression vehicles for production of a recombinant protein include plasmids and other vectors. For instance, suitable vectors for the expression of a fusion polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

In another embodiment, the nucleic acid encoding the heat protein fusion polypeptide is operably linked to a bacterial promoter, e.g., the anaerobic *E. coli*, NirB promoter or the *E. coli* lipoprotein llp promoter, described, e.g., in Inouye et al. (1985) *Nucl. Acids Res.* 13:3101; *Salmonella* pagC promoter (Miller et al., supra), *Shigella* ent promoter (Schmitt and Payne, *J. Bacteriol.* 173:816 (1991)), the tet promoter on Tn10 (Miller et al., supra), or the ctx promoter of *Vibrio cholera*. Any other promoter can be used. The bacterial promoter can be a constitutive promoter or an inducible promoter. An exemplary inducible promoter is a promoter which is inducible by iron or in iron-limiting conditions. In fact, some bacteria, e.g., intracellular organisms, are believed to encounter iron-limiting conditions in the host cytoplasm. Examples of iron-regulated promoters of FepA and TonB are known in the art and are described, e.g., in the following references: Headley, V. et al. (1997) *Infection & Immunity* 65:818; Ochsner, U. A. et al. (1995) *Journal of Bacteriology* 177:7194; Hunt, M. D. et al. (1994) *Journal of Bacteriology* 176:3944; Svinarich, D. M. and S. Palchaudhuri. (1992) *Journal of Diarrhoeal Diseases Research* 10:139; Prince, R. W. et al. (1991) *Molecular Microbiology* 5:2823; Goldberg, M. B. et al. (1990) *Journal of Bacteriology* 172:6863; de Lorenzo, V. et al. (1987) *Journal of Bacteriology* 169:2624; and Hantke, K. (1981) *Molecular & General Genetics* 182:288.

A plasmid preferably comprises sequences required for appropriate transcription of the nucleic acid in bacteria, e.g., a transcription termination signal. The vector can further comprise sequences encoding factors allowing for the selection of bacteria comprising the nucleic acid of interest, e.g., gene encoding a protein providing resistance to an antibiotic, sequences required for the amplification of the nucleic acid, e.g., a bacterial origin of replication.

In another embodiment, a signal peptide sequence is added to the construct, such that the fusion polypeptide is secreted from cells. Such signal peptides are well known in the art.

In one embodiment, the powerful phage T5 promoter, that is recognized by *E. coli* RNA polymerase is used together with a lac operator repression module to provide tightly regulated, high level expression or recombinant proteins in *E. coli*. In this system, protein expression is blocked in the presence of high levels of lac repressor.

In one embodiment, the DNA is operably linked to a first promoter and the bacterium further comprises a second DNA encoding a first polymerase which is capable of mediating transcription from the first promoter, wherein the DNA encoding the first polymerase is operably linked to a second promoter. In a preferred embodiment, the second promoter is a bacterial promoter, such as those delineated above. In an even more preferred embodiment, the polymerase is a bacteriophage polymerase, e.g., SP6, T3, or T7 polymerase and the first promoter is a bacteriophage promoter, e.g., an SP6, T3, or T7 promoter, respectively. Plasmids comprising bacteriophage promoters and plasmids encoding bacteriophage polymerases can be obtained commercially, e.g., from Promega Corp.(Madison, Wis.) and InVitrogen (San Diego, Calif.), or can be obtained directly from the bacteriophage using standard recombinant DNA techniques (J. Sambrook, E. Fritsch, T. Maniatis, Molecular Cloning: A Laboratory Manual, Cold Spring Laboratory Press, 1989). Bacteriophage polymerases and promoters are further described, e.g., in the following references: Sagawa, H. et al. (1996) *Gene* 168:37; Cheng, X. et al. (1994) *PNAS USA* 91:4034; Dubendorff, J. W. and F. W. Studier (1991) *Journal of Molecular Biology* 219:45; Bujarski, J. J. and P. Kaesberg (1987) *Nucleic Acids Research* 15:1337; and Studier, F. W. et al. (1990) *Methods in Enzymology* 185:60). Such plasmids can further be modified according to the specific embodiment of the heat shock protein fusion to be expressed.

In another embodiment, the bacterium further comprises a DNA encoding a second polymerase which is capable of mediating transcription from the second promoter, wherein the DNA encoding the second polymerase is operably linked to a third promoter. The third promoter may be a bacterial promoter. However, more than two different polymerases and promoters could be introduced in a bacterium to obtain high levels of transcription. The use of one or more polymerases for mediating transcription in the bacterium can provide a significant increase in the amount of polypeptide in the bacterium relative to a bacterium in which the DNA is directly under the control of a bacterial promoter. The selection of the system to adopt will vary depending on the specific use, e.g., on the amount of protein that one desires to produce.

Generally, a nucleic acid encoding a fusion protein is introduced into a host cell, such as by transfection, and the host cell is cultured under conditions allowing expression of the fusion protein. Methods of introducing nucleic acids into prokaryotic and eukaryotic cells are well known in the art. Suitable media for mammalian and prokaryotic host cell culture are well known in the art. Generally, the nucleic acid encoding the subject fusion protein is under the control of an inducible promoter, which is induced once the host cells comprising the nucleic acid have divided a certain number of times. For example, where a nucleic acid is under the control of a beta-galactose operator and repressor, isopropyl beta-D-thiogalactopyranoside (IPTG) is added to the culture when the bacterial host cells have attained a density of about $OD_{600}$ 0.45-0.60. The culture is then grown for some more time to give the host cell the time to synthesize the protein. Cultures are then typically frozen and may be stored frozen for some time, prior to isolation and purification of the protein.

When using a prokaryotic host cell, the host cell may include a plasmid which expresses an internal T7 lysozyme, e.g., expressed from plasmid pLysSL (see Examples). Lysis of such host cells liberates the lysozyme which then degrades the bacterial membrane.

Other sequences that may be included in a vector for expression in bacterial or other prokaryotic cells include a synthetic ribosomal binding site; strong transcriptional terminators, e.g., $t_0$ from phage lambda and $t_4$ from the rrnB operon in *E. coli*, to prevent read through transcription and ensure stability of the expressed protein; an origin of replication, e.g., ColE1; and beta-lactamase gene, conferring ampicillin resistance.

Other host cells include prokaryotic host cells. Even more preferred host cells are bacteria, e.g., *E. coli*. Other bacteria that can be used include *Shigella* spp., *Salmonella* spp., *Listeria* spp., *Rickettsia* spp., *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Vibrio* spp., *Bacillus* spp., and *Erysipelothrix* spp. Most of these bacteria can be obtained from the American Type Culture Collection (ATCC; 10801 University Blvd., Manassas, Va. 20110-2209).

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal comprising pBlueBac III).

In another variation, protein production may be achieved using in vitro translation systems. In vitro translation systems are, generally, a translation system which is a cell-free extract comprising at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. An RNA nucleotide for in vitro translation may be produced using methods known in the art. In vitro transcription and translation may be coupled in a one-pot reaction to produce proteins from one or more isolated DNAs.

When expression of a carboxy terminal fragment of a protein is desired, i.e. a truncation mutant, it may be necessary to add a start codon (ATG) to the oligonucleotide fragment comprising the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant proteins in a host which produces MAP (e.g., *E. coli* or CM89 or *S. cerevisiae*), or in vitro by use of purified MAP (e.g., procedure of Miller et al.).

In cases where plant expression vectors are used, the expression a heat shock protein fusion may be driven by any of a number of promoters. For example, viral promoters such as the 35S RNA and 19S RNA promoters of CaMV (Brisson et al., 1984, Nature, 310:511-514), or the coat protein promoter of TMV (Takamatsu et al., 1987, EMBO J., 6:307-311) may be used; alternatively, plant promoters such as the small subunit of RUBISCO (Coruzzi et al., 1994, EMBO J., 3:1671-1680; Broglie et al., 1984, Science, 224: 838-843); or heat shock promoters, e.g., soybean Hsp 17.5-E or Hsp 17.3-B (Gurley et al., 1986, Mol. Cell. Biol., 6:559-565) may be used. These constructs can be introduced into plant cells using Ti plasmids, Ri plasmids, plant virus vectors; direct DNA transformation; microinjection, electroporation, etc. For reviews of such techniques see, for example, Weissbach & Weissbach, 1988, Methods for Plant Molecular Biology, Academic Press, New York, Section VIII, pp. 421-463; and Grierson & Corey, 1988, Plant Molecular Biology, 2d Ed., Blackie, London, Ch. 7-9.

An alternative expression system which can be used to express a protein tag or fusion protein comprising a protein tag is an insect system. In one such system, *Autographa californica* nuclear polyhedrosis virus (AcNPV) is used as a vector to express foreign genes. The virus grows in *Spodoptera frugiperda* cells. The PGHS-2 sequence may be cloned into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol., 46:584, Smith, U.S. Pat. No. 4,215,051).

In a specific embodiment of an insect system, the DNA encoding the heat shock protein fusion protein is cloned into the pBlueBacIII recombinant transfer vector (Invitrogen, San Diego, Calif.) downstream of the polyhedrin promoter and transfected into Sf9 insect cells (derived from *Spodoptera frugiperda* ovarian cells, available from Invitrogen, San Diego, Calif.) to generate recombinant virus. After plaque purification of the recombinant virus high-titer viral stocks are prepared that in turn would be used to infect Sf9 or High Five™ (BTI-TN-5B1-4 cells derived from *Trichoplusia ni* egg cell homogenates; available from Invitrogen, San Diego, Calif.) insect cells, to produce large quantities of appropriately post-translationally modified subject protein.

In other embodiments, the heat shock protein fusion and biotin-binding protein are produced separately and then linked, e.g. covalently linked, to each other. For example, a heat shock protein fusion and biotin-binding protein are produced separately in vitro, purified, and mixed together under conditions under which the tag will be able to be linked to the protein of interest. For example, the heat shock protein and/or the biotin-binding protein can be obtained (isolated) from a source in which it is known to occur, can be produced and harvested from cell cultures, can be produced by cloning and expressing a gene encoding the desired heat shock protein fusion, or can be synthesized chemically. Furthermore, a nucleic acid sequence encoding the desired heat shock protein fusion can be synthesized chemically. Such mixtures of conjugated proteins may have properties different from single fusion proteins.

Linkers (also known as "linker molecules" or "cross-linkers") may be used to conjugate a heat shock protein and biotin-binding protein. Linkers include chemicals able to react with a defined chemical group of several, usually two, molecules and thus conjugate them. The majority of known cross-linkers react with amine, carboxyl, and sulfhydryl groups. The choice of target chemical group is crucial if the group may be involved in the biological activity of the proteins to be conjugated. For example, maleimides, which react with sulfhydryl groups, may inactivate Cys-comprising proteins that require the Cys to bind to a target. Linkers may be homofunctional (comprising reactive groups of the same type), heterofunctional (comprising different reactive groups), or photoreactive (comprising groups that become reactive on illumination).

Linker molecules may be responsible for different properties of the conjugated compositions. The length of the linker should be considered in light of molecular flexibility during the conjugation step, and the availability of the conjugated molecule for its target (cell surface molecules and the like.) Longer linkers may thus improve the biological activity of the compositions of the present invention, as well as the ease of preparation of them. The geometry of the linker may be used to orient a molecule for optimal reaction with a target. A linker with flexible geometry may allow the cross-linked proteins to conformationally adapt as they bind other proteins. The nature of the linker may be altered for other various purposes. For example, the aryl-structure of MBuS was found less immunogenic than the aromatic spacer of MBS. Furthermore, the hydrophobicity and functionality of the linker molecules may be controlled by the physical properties of component molecules. For example, the hydrophobicity of a polymeric linker may be controlled by the order of monomeric units along the polymer, e.g. a block polymer in which there is a block of hydrophobic monomers interspersed with a block of hydrophilic monomers.

The chemistry of preparing and utilizing a wide variety of molecular linkers is well-known in the art and many premade linkers for use in conjugating molecules are commercially available from vendors such as Pierce Chemical Co., Roche Molecular Biochemicals, United States Biological, and the like.

The prepared and/or isolated heat shock protein fused to a biotin-binding protein is to be administered to a subject in conjunction with the desired biotinylated components, sufficient to form a non-covalent association of the biotin moiety with the biotin-binding protein. The heat shock protein fusion and the biotinylated component or components may be administered simultaneously or sequentially. If administered simultaneously, the heat shock protein fusion and the biotinylated component or components may be administered as a mixture or as a noncovalent complex. If administered as a noncovelent complex, a heat shock protein fused to a biotin-binding protein may be noncovalently bound to the desired biotinylated components either in vitro or in vivo once prepared and/or isolated.

The noncovalent complex may be produced by contacting the heat shock protein fused to a biotin-binding protein with the biotinylated components, under conditions sufficient to promote the binding of the biotin-binding protein with biotin, which conditions are known in the art.

Genes for various heat shock proteins have been cloned and sequenced, and which may be used to obtain a heat shock protein fusion, including, but not limited to, gp96 (human: Genebank Accession No. X15187; Maki et al., Proc. Natl. Acad. Sci. U.S.A. 87:5658-5562 (1990); mouse:

Genebank Accession No. M16370; Srivastava et al., Proc. Natl. Acad. Sci. U.S.A. 84:3807-3811 (1987)), BiP (mouse: Genebank Accession No. U16277; Haas et al., Proc. Natl. Acad. Sci. U.S.A. 85:2250-2254 (1988); human: Genebank Accession No. M19645; Ting et al., DNA 7:275-286 (1988)), hsp70 (mouse: Genebank Accession No. M35021; Hunt et al., Gene 87:199-204 (1990); human: Genebank Accession No. M24743; Hunt et al, Proc. Natl. Acad. Sci. U.S.A. 82:6455-6489 (1995)), and hsp40 (human: Genebank Accession No. D49547; Ohtsuka K., Biochem. Biophys. Res. Commun. 197:235-240 (1993)).

The heat shock protein fused to a biotin-binding protein may be non-covalently bound to the biotinylated component.

The component to be administered in conjunction with the heat shock protein comprising the protein, cell, or virus may be conjugated to biotin by means such as is known in the art. Prior to conjugation to biotin, the protein, cell, or virus may be produced and/or isolated using methods known in the art. Recombinant techniques may be employed in much the same way as described herein for the heat shock protein fusion. Once the component is produced and/or isolated, a biotin molecule or molecules may be conjugated directly to a protein, cell, or virus. Biotin may also be conjugated indirectly through a linker to said protein, cell, or virus. Biotin is to be conjugated to a region that sterically allows for the interaction of biotin with the biotin-binding protein. Biotinylation kits and reagents may be purchased from Pierce (Rockford, Ill.) and used to generate the biotinylated components described herein.

The sequences of many different antigens can be cloned and characterized by DNA sequence analysis and included in the compositions provided herein. Bacterial vectors containing complete or partial cellular or viral genomes or antigens may be obtained from various sources including, for example, the American Tissue Culture Collection (ATCC). Additional antigens which may be used can be isolated and typed by the methods previously established for this purpose, which methods are well known in the art.

Methods of Using the Heat Shock Protein Fusion and Biotinylated Components

The heat shock protein fusion and biotinylated components described herein can be administered to a subject to induce or enhance that subject's immune response, particularly a cell-mediated cytolytic response, against a cell expressing an antigen against which the biotinylated components are directed. The fusion protein may simply enhance the immune response (thus serving as an immunogenic composition), or confer protective immunity (thus serving as a vaccine).

Thus, the heat shock protein fusion and biotinylated components produced as described above may be purified to a suitable purity for use as a pharmaceutical composition. Generally, purified compositions will have one species that comprises more than about 85 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a heat shock protein fusion and biotinylated components, or a non-covalent complex of the same, using standard techniques for purification, for example, immunoaffinity chromotography, size exclusion chromatography, etc. in light of the teachings herein. Purity of a protein may be determined by a number of methods known to those of skill in the art, including for example, amino-terminal amino acid sequence analysis, gel electrophoresis and mass-spectrometry analysis.

Accordingly, provided are pharmaceutical compositions comprising the above-described heat shock protein fusion and biotinylated components, or a non-covalent complex of the same. In one aspect, provided are pharmaceutically acceptable compositions which comprise a therapeutically-effective amount of one or more of the pharmaceutical compositions described herein, formulated together with one or more pharmaceutically acceptable carriers (additives) and/or diluents. In another aspect, in certain embodiments, the pharmaceutical compositions may be administered as such or in admixtures with pharmaceutically acceptable carriers and may also be administered in conjunction with other agents. Conjunctive (combination) therapy thus includes sequential, simultaneous and separate, or co-administration in a way that the therapeutic effects of the first administered one has not entirely disappeared when the subsequent is administered.

The heat shock protein fusion and biotinylated components, or a non-covalent complex of the same, as described herein can be administered to a subject in a variety of ways. The routes of administration include systemic, peripheral, parenteral, enteral, topical, and transdermal (e.g., slow release polymers). Any other convenient route of administration can be used, for example, infusion or bolus injection, or absorption through epithelial or mucocutaneous linings. In addition, the compositions described herein can contain and be administered together with or without other pharmacologically acceptable components such as biologically active agents (e.g., adjuvants such as alum), surfactants (e.g., glycerides), excipients (e.g., lactose), carriers, diluents and vehicles. Furthermore, the compositions can be used ex vivo as a means of stimulating white blood cells obtained from a subject to elicit, expand and propagate antigen-specific immune cells in vitro that are subsequently reintroduced into the subject.

Further, a heat shock protein fusion protein can be administered by in vivo expression of a nucleic acid encoding such protein sequences into a human subject. Expression of such a nucleic acid and contact with biotinylated components can also be achieved ex vivo as a means of stimulating white blood cells obtained from a subject to elicit, expand and propagate antigen-specific immune cells in vitro that are subsequently reintroduced into the subject. Expression vectors suitable for directing the expression of heat shock protein fusion proteins can be selected from the large variety of vectors currently used in the field. Preferred will be vectors that are capable of producing high levels of expression as well as are effective in transducing a gene of interest. For example, recombinant adenovirus vector pJM17 (All et al., Gene Therapy 1:367-84 (1994); Berkner K. L., Biotechniques 6:616-24 1988), second generation adenovirus vectors DE1/DE4 (Wang and Finer, Nature Medicine 2:714-6 (1996)), or adeno-associated viral vector AAV/Neo (Muro-Cacho et al., J. Immunotherapy 11:231-7 (1992)) can be used. Furthermore, recombinant retroviral vectors MFG (Jaffee et al., Cancer Res. 53:2221-6 (1993)) or LN, LNSX, LNCX, LXSN (Miller and Rosman, Biotechniques 7:980-9 (1989)) can be employed. Herpes simplex virus-based vectors such as pHSV1 (Geller et al., Proc. Nat'l Acad. Sci. 87:8950-4 (1990) or vaccinia viral vectors such as MVA (Sutter and Moss. Proc. Nat'l Acad. Sci. 89:10847-51 (1992)) can serve as alternatives.

Frequently used specific expression units including promoter and 3' sequences are those found in plasmid cDNA3 (Invitrogen), plasmid AH5, pRC/CMV (Invitrogen), pCMU II (Paabo et al., EMBO J. 5:1921-1927 (1986)), pZip-Neo SV (Cepko et al., Cell 37:1053-1062 (1984)) and pSRa (DNAX, Palo Alto, Calif.). The introduction of genes into expression units and/or vectors can be accomplished using genetic engineering techniques, as described in manuals like Molecular Cloning and Current Protocols in Molecular Biology (Sambrook, J., et al., Molecular Cloning, Cold Spring Harbor Press (1989); Ausubel, F. M. et al., Current Protocols in Molecular Biology, Greene Publishing Associates and Wiley-Interscience (1989)). A resulting expressible nucleic acid can be introduced into cells of a human subject by any method capable of placing the nucleic acid into cells in an expressible form, for example as part of a viral vector such as described above, as naked plasmid or other DNA, or encapsulated in targeted liposomes or in erythrocyte ghosts (Friedman, T., Science, 244:1275-1281 (1989); Rabinovich, N. R. et al., Science. 265:1401-1404 (1994)). Methods of transduction include direct injection into tissues and tumors, liposomal transfection (Fraley et al., Nature 370:111-117 (1980)), receptor-mediated endocytosis (Zatloukal et al., Ann. N.Y. Acad. Sci. 660:136-153 (1992)), and particle bombardment-mediated gene transfer (Eisenbraun et al., DNA & Cell. Biol. 12:791-797 (1993)).

The amount of heat shock protein fusion and biotinylated components, or a non-covalent complex of the same, in the compositions of the present invention is an amount which produces an effective immunostimulatory response in a subject. An effective amount is an amount such that when administered, it induces an immune response. In addition, the amount of heat shock protein fusion and biotinylated components, or a non-covalent complex of the same, administered to the subject will vary depending on a variety of factors, including the heat shock protein fusion and biotinylated component employed, the size, age, body weight, general health, sex, and diet of the subject as well as on its general immunological responsiveness. Adjustment and manipulation of established dose ranges are well within the ability of those skilled in the art. For example, the amount of heat shock protein fusion, biotinylated components, or a non-covalent complex of the sam, ecan be from about 1 microgram to about 1 gram, preferably from about 100 microgram to about 1 gram, and from about 1 milligram to about 1 gram. An effective amount of a composition comprising an expression vector is an amount such that when administered, it induces an immune response against the antigen against which the pharmaceutical composition is directed. Furthermore, the amount of expression vector administered to the subject will vary depending on a variety of factors, including the heat shock protein fusion expressed, the size, age, body weight, general health, sex, and diet of the subject, as well as on its general immunological responsiveness. Additional factors that need to be considered are the route of application and the type of vector used. For example, when prophylactic or therapeutic treatment is carried out with a viral vector containing a nucleic acid encoding heat shock protein fusion, the effective amount will be in the range of $10^4$ to $10^{12}$ helper-free, replication-defective virus per kg body weight, preferably in the range of $10^5$ to $10^{11}$ virus per kg body weight and most preferably in the range of $10^6$ to $10^{10}$ virus per kg body weight.

Determination of an effective amount of fusion protein and biotinylated components, or a non-covalent complex of the same, for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the proteins and/or strains of the invention may be administered in about 1 to 3 doses for a 1-36 week period. Preferably, 3 doses are administered, at intervals of about 3-4 months, and booster vaccinations may be given periodically thereafter. Alternate protocols may be appropriate for individual patients. A suitable dose is an amount of protein or strain that, when administered as described above, is capable of raising an immune response in an immunized patient sufficient to protect the patient from the condition or infection for at least 1-2 years.

The compositions may also include adjuvants to enhance immune responses. In addition, such proteins may be further suspended in an oil emulsion to cause a slower release of the proteins in vivo upon injection. The optimal ratios of each component in the formulation may be determined by techniques well known to those skilled in the art.

Any of a variety of adjuvants may be employed in the vaccines of this invention to enhance the immune response. Most adjuvants contain a substance designed to protect the antigen from rapid catabolism, such as aluminum hydroxide or mineral oil, and a specific or nonspecific stimulator of immune responses, such as lipid A, or Bortadella pertussis. Suitable adjuvants are commercially available and include, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A, quil A, SBAS1c, SBAS2 (Ling et al., 1997, Vaccine 15:1562-1567), SBAS7, Al(OH)$_3$ and CpG oligonucleotide (WO96/02555).

In the vaccines of the present invention, the adjuvant may induce a Th1 type immune response. Suitable adjuvant systems include, for example, a combination of monophosphoryl lipid A, preferably 3-de-O-acylated monophosphoryl lipid A (3D-MPL) together with an aluminum salt. An enhanced system involves the combination of a monophosphoryl lipid A and a saponin derivative, particularly the combination of 3D-MLP and the saponin QS21 as disclosed in WO 94/00153, or a less reactogenic composition where the QS21 is quenched with cholesterol as disclosed in WO 96/33739. Previous experiments have demonstrated a clear synergistic effect of combinations of 3D-MLP and QS21 in the induction of both humoral and Th1 type cellular immune responses. A particularly potent adjuvant formation involving QS21, 3D-MLP and tocopherol in an oil-in-water emulsion is described in WO 95/17210 and may comprise a formulation.

Kits

The present invention provides kits for expressing or administering a heat shock protein fused to a biotin-binding protein. Such kits may be comprised of nucleic acids encoding heat shock protein fused to a biotin-binding protein. The nucleic acids may be included in a plasmid or a vector, e.g., a bacterial plasmid or viral vector. Other kits comprise a heat shock protein fused to a biotin-binding protein. Furthermore, the present invention provides kits for producing and/or purifying a heat shock protein fused to a biotin-binding protein. Such kits may optionally include biotinylated components or biotinylation reagents as described herein.

The present invention provides kits for preventing or treating infectious or malignant disease in a patient. For example, a kit may comprise one or more pharmaceutical compositions as described above and optionally instructions for their use. In still other embodiments, the invention provides kits comprising one more pharmaceutical composition and one or more devices for accomplishing administration of such compositions.

Kit components may be packaged for either manual or partially or wholly automated practice of the foregoing methods. In other embodiments involving kits, instructions for their use may be provided.

EXEMPLIFICATION

The invention now being generally described, it will be more readily understood by reference to the following examples which are included merely for purposes of illustration of certain aspects and embodiments of the present invention, and are not intended to limit the invention in any way.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Example 1 i) Production of MTBhsp70

MTBhsp70 was subcloned into the expression vector pET45b(+) by first modifying the vector to introduce the desired restriction site SfiI. This modification allows introduction of the MTBhsp70 protein at the NotI/XhoI site and other proteins such as scFvs, antigens, Avidin, etc. at the SfiI/NotI site (FIG. 1). This particular approach can be modified to introduce the desired proteins at the C-terminal of MTBhsp70. Using the MTBhsp70 plasmid provided by Dr. Richard Young, restriction sites NotI and XhoI were introduced at the 5' and 3' end respectively as described in FIG. 2.

Figure 3:
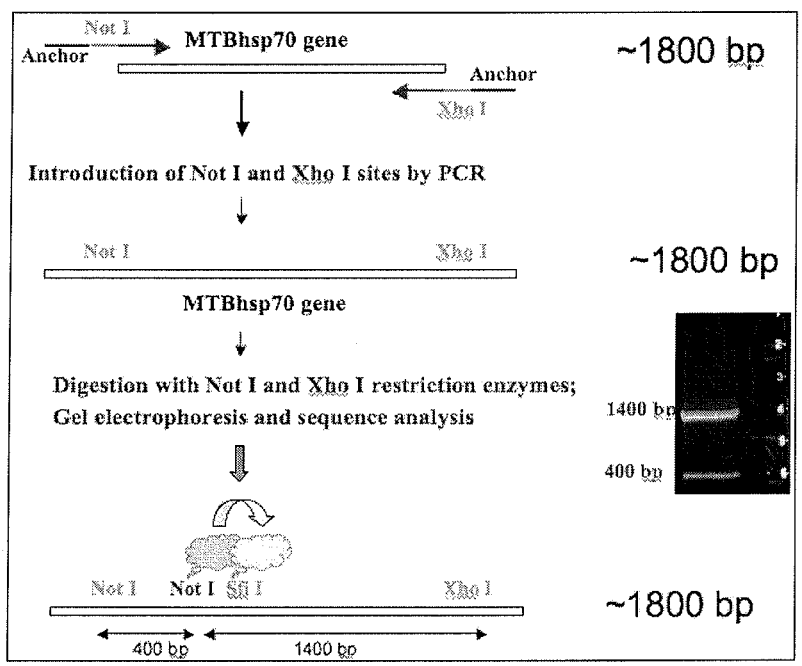
FIG. 3 shows digestion of the amplified MTBhsp70 with NotI and XhoI yielding 2 bands as shown on the gel picture. Sequencing analyses established the presence of internal NotI and SfiI sites.

Digestion of the amplified MTBhsp70 fragment shown in lane 1 of FIG. 2 with the restriction enzymes NotI and XhoI unexpectedly revealed 2 bands (FIG. 3). Sequencing analyses revealed that MTBhsp70 contains internal NotI and SfiI restriction sites. These were removed using the strategy depicted in FIG. 4. The resulting MTBhsp70 pET-45b(+) construct was then used to transform competent BL21(DE3) bacteria. Expression of MTBhsp70 was induced by adding 1 mM IPTG. Cells were grown in LB medium at 37° C. to an $OD_{600}$ of 0.5. Cells were spun down and suspended in LB medium containing 1 mM IPTG and growth continued for 4 hours at the indicated temperature. Cells were fractionated and aliquots were run on SDS-PAGE and proteins were stained with Coomassie Blue. When induced cells were grown at 37° C. the majority of the MTBhsp70 protein was found in insoluble inclusion bodies. By reducing the growth temperature post induction to 30° C., large amounts of soluble MTBhsp70 were produced. The MTBhsp70 protein found in the soluble and periplasmic fractions of BL21 (DE3) grown at 30° C. was successfully purified by metal affinity chromatography (MAC) using Cobalt spin columns. Cells were grown at 37° C. to an $OD_{600}$ of 0.5 and then spun down. Cells were suspended in growth media containing 1 mM IPTG and allowed to grow for 4 hours at 30° C. Cells were fractionated according to standard methods consisting of solubilization with B-PER reagent from Pierce.

ii) Production of MTBhsp70-Fusion Proteins

In order to demonstrate the immunostimulatory properties of MTBhsp70-fusion proteins, an Ovalbumin peptide-MTBhsp70 and two scFv-MTBhsp70 fusion products were constructed.

a. Ova-257-264-MTBhsp70 fusion protein. Dr. Young's group established that the Ovalbumin's immunodominant peptide consists of residues 257-264 (SIINFEKL) (SEQ ID NO: 4). This peptide was fused to the N-terminal region of MTBhsp70 by digesting the MTBhsp70 pET-45b(+) plasmid with SfiI and NotI and introducing a linker coding for the immunodominant peptide that is also digested with SfiI and NotI (FIG. 5). Upon ligation, a number of colonies were obtained, and their identities were confirmed by sequencing (FIG. 6). As observed with MTBhsp70, induction of Ova-257-264-MTBhsp70 is optimum when the growth temperature, post-IPTG induction, is kept at 30° C. Successful expression of Ova254-264-MTBhsp70 was obtained in the soluble fraction of BL21(DE3).

b. scFv-MTBhsp70 fusion proteins. scFvs were fused to the N-terminal of MTBhsp70. A human combinatorial scFv phage display library was constructed and used it to select Ovalbumin specific scFvs. The other scFv, MOV18, is specific for the high affinity Folate Receptor expressed on ovarian cancer cells. The cloning method is similar to the approach used for the introduction of the $Ova_{254-264}$ peptide at the N-terminal of MTBhsp70. The SfiI/NotI scFv portion was purified from their respective plasmids followed by ligation into the SfiI/NotI digested expression vector MTBhsp70 pET-45b (+). The anti-Ovalbumin scFvs had several non-sense mutations that had to be removed by site directed mutagenesis. However, upon induction of bacteria carrying both constructs, it was found that induction with IPTG resulted in the fusion proteins being expressed in inclusion bodies.

iii) Production of Avidin-Linker-MTBhsp70

Figure 7:
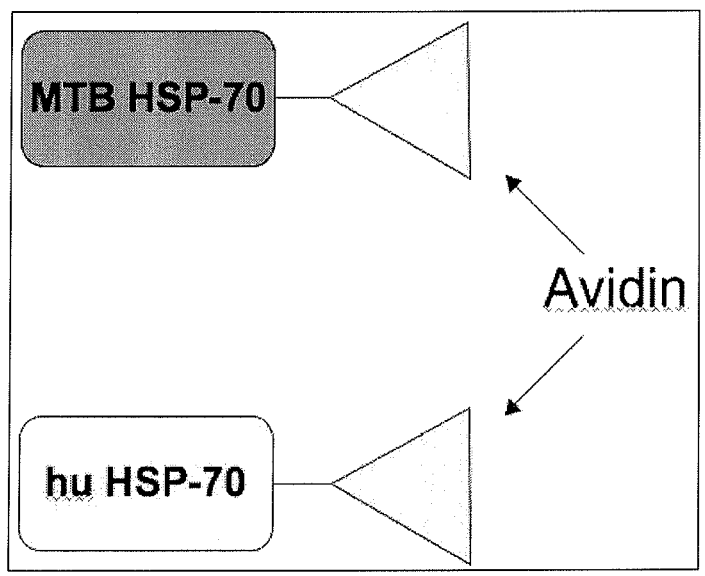
FIG. 7 is a schematic structure of heat shock protein fusions of a self-assembling pharmaceutical composition. Depicted are heat shock proteins MTB HSP-70 and human HSP-70 each separately fused to Avidin as the biotin-binding protein.
Figure 8:
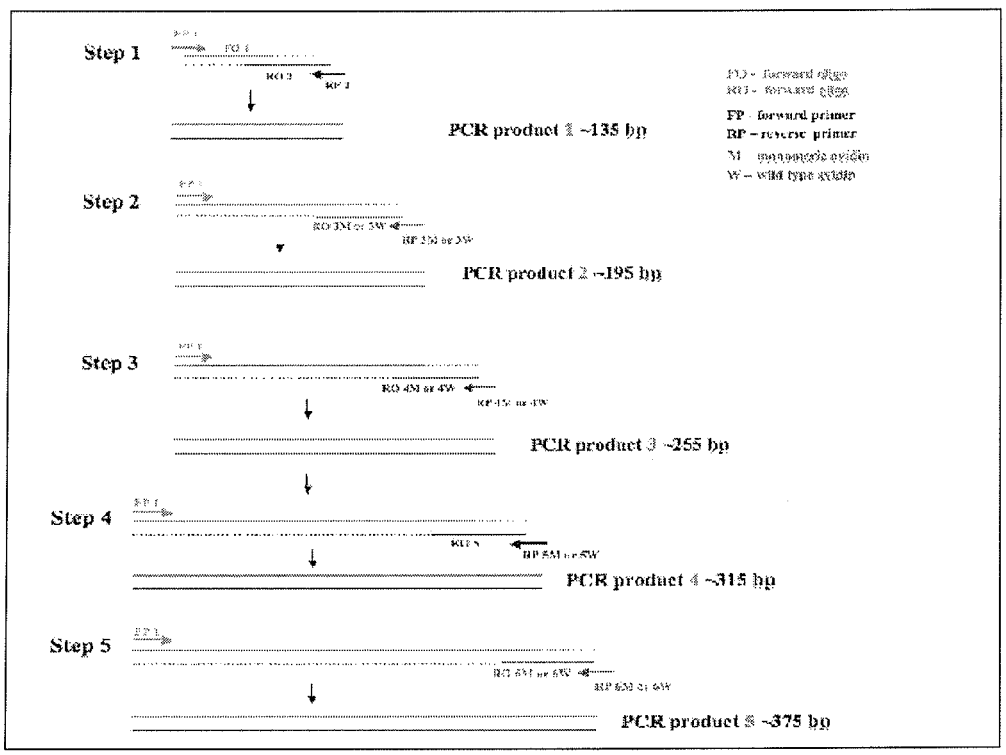
FIG. 8 depicts a strategy for the assembly of wild-type and monomeric Avidin.

A fusion of Avidin to a linker element and to MTBhsp70 may be used for the production of a self-assembling vaccine. This is illustrated in FIG. 7 where the linker portion is illustrated as a line between Avidin and heat shock proteins. Avidin is a homo tetrameric glycosylated protein with a molecular weight of 68,000 (thus each subunit is 17,000 dalton). The wild-type (tetrameric) or the monomeric form described by Dr. Markku S. Kulomaa may be produced and used as provided herein. These molecules are described according to the scheme of FIG. 8. The monomeric form of avidin differs from the wild-type at 5 amino acid positions.

This is illustrated in FIG. 9. A series of primers and linkers were used to assemble each Avidin construct.

Figure 11:
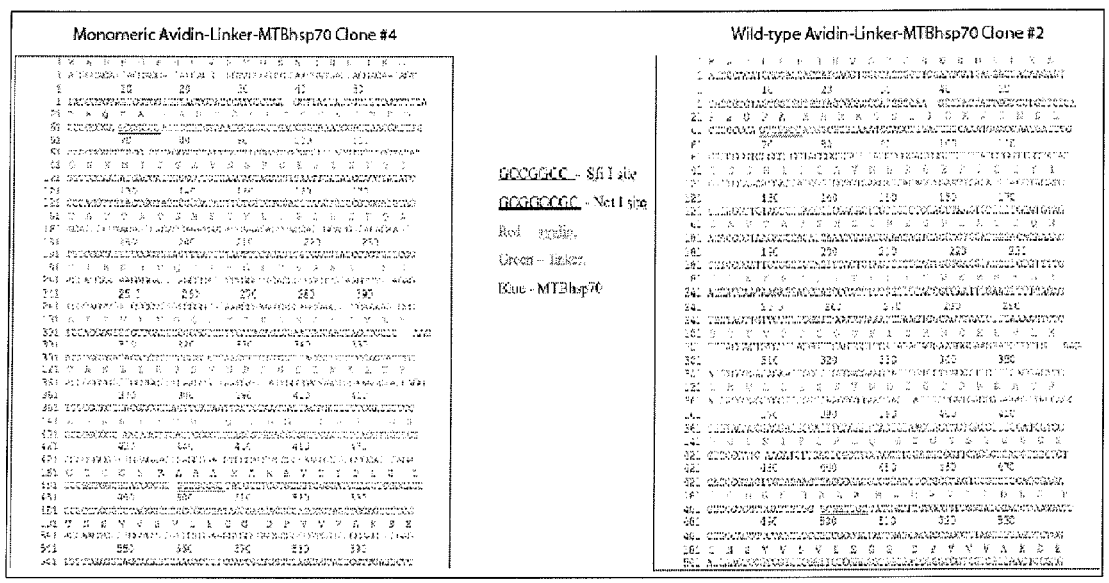
FIG. 11 illustrates monomeric/Wild-type Avidin-Linker-MTBhsp70 sequences with partial MTBhsp70 sequence shown.
Figure 12:
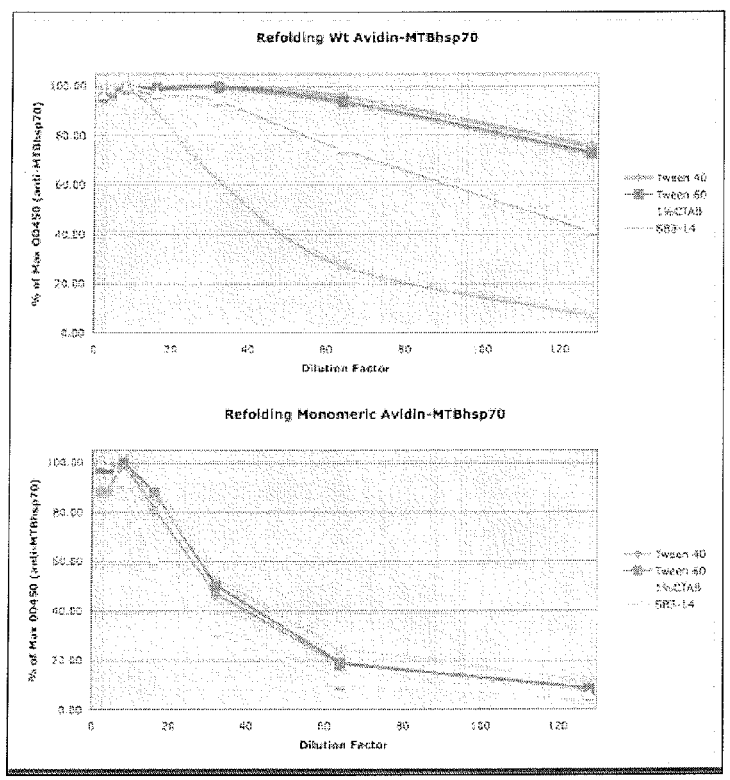
FIG. 12 shows refolding of Avidin-Linker-MTBhsp70 proteins found in inclusion bodies.
Figure 13:
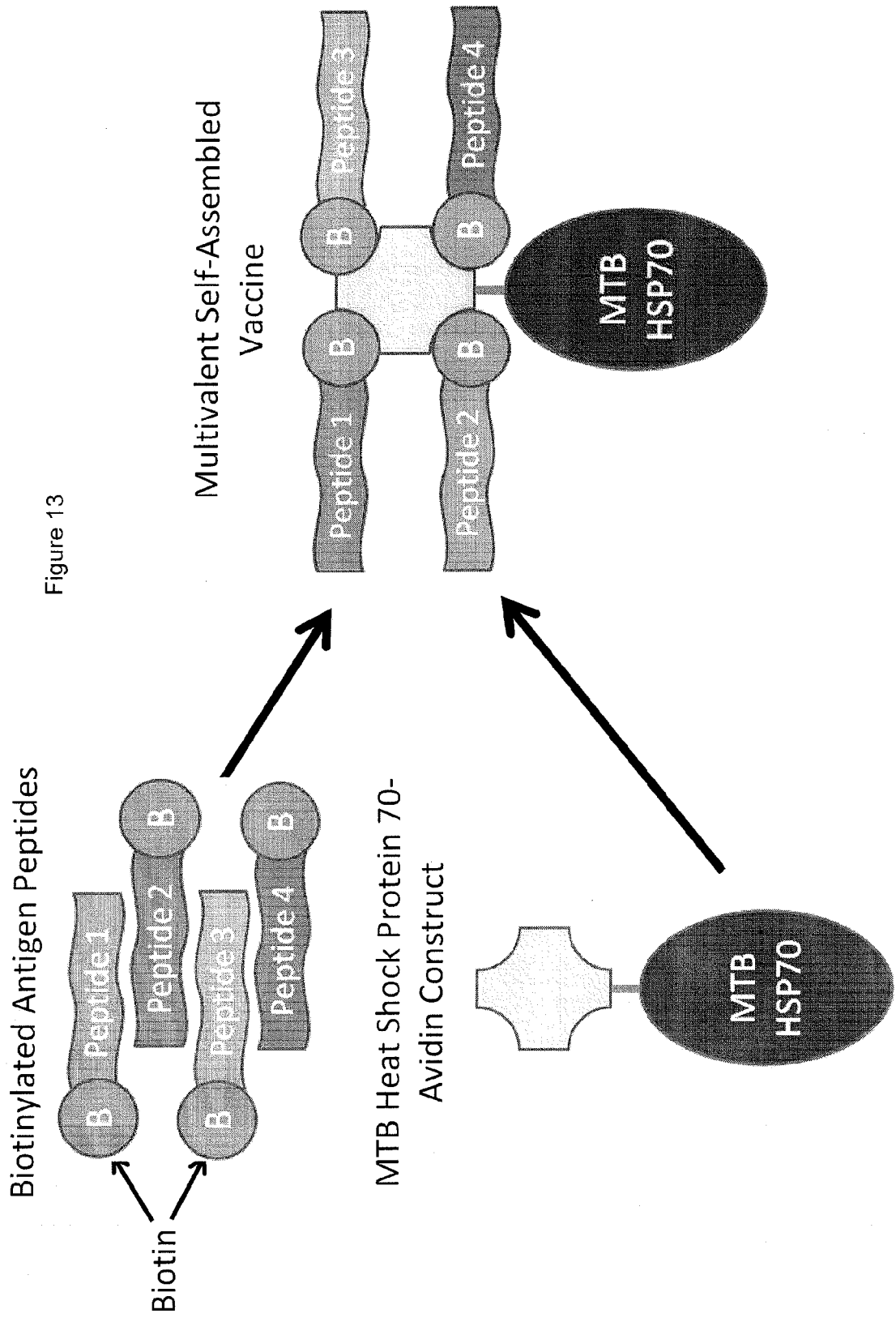
FIG. 13 is a schematic of a multivalent self-assembly of a heat shock protein fusion (shown as a fusion protein of MTb HSP70 and Avidin) and four biotinylated components (shown as biotinylated peptides 1-4) to form a multivalent self-assembled vaccine.
Figure 15:
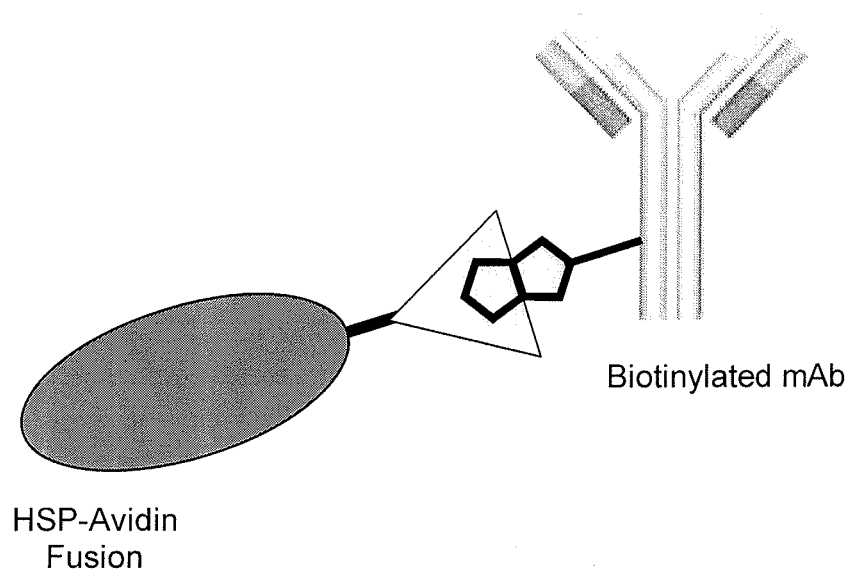
FIG. 15 is a depiction of a self-assembled vaccine of a heat shock fusion protein and a biotinylated component. The heat shock fusion protein here is shown as an HSP-Avidin Fusion, and the biotinylated component is shown as a biotinylated monoclonal antibody (Biotinylated mAb).

Minor mutations were corrected by PCR based mutagenesis. This is illustrated in FIG. 10, which shows two changes that were made to monomeric avidin (clone M1). Both monomeric and wild-type Avidin-linker-MTBhsp70 constructs were successfully obtained as shown in FIG. 11. Both constructs lead to abundant protein production upon induction with IPTG in *E. coli* BL21(DE3). However, the induced Avidin-linker-MTBhsp70 proteins are found mostly in inclusion bodies, which may be solubilized, denatured and refolded.

Following denaturation with guadinium hydrochloride and DTT, the proteins are diluted in 4 different refolding buffers (1) Tween 40, Cystine; 2) Tween 60, Cystine; 3) CTAB, Cystine; 4) SB3-14, Cystine) containing cystine to quench excess DTT. After addition of 3% CA solution the proteins are allowed to refold overnight at room temperature. To assess the level of refolding, refolded protein aliquots were added to biotin-coated wells. Thus, properly refolded Avidin-Linker-MTBhsp70 proteins would bind tightly to the bottom of those wells. The amount of plate-bound proteins were determined by using a monoclonal antibody against MTBhsp70 followed by the detection of bound anti-MTBhsp70 using Horse Radish Peroxidase (HRP) labeled Goat anti mouse (H+L) antibodies. The optical density was recorded at 450 nm and expressed the results as percent maximum signal. The results are depicted in FIG. 12. Proper refolding of each protein may include subjected each protein to different conditions. In order to assess the biological activity of the refolded MTBhsp70 portion of these proteins, their ability to hydrolyze ATP may be measured. Furthermore, chemotactic effects of MTBhsp70 on THP-1 cells may be determined.

Example 2

The self-assembly and biological activities of m/wAvidin-Linker-N-MTBhsp70 proteins may be determined as follows:

1) Determination of ATPase activity. The N-terminal portion of MTBhsp70 is known to hydrolyze ATP under certain assay conditions. The proper refolding of our m/wAvidin-Linker-N-MTBhsp70 proteins may be assessed by comparing their ATPase activity to that of a commercial preparation and our own MTBhsp70.
2) Determination of chemotactic activity/induction of chemokine production. Another assay of proper refolding of the MTBhsp70 portion of our m/wAvidin-Linker-N-MTBhsp70 proteins is their successful induction of CC chemokines from the cell line THP-1. Exposure of the monocyte cell line THP-1 to MTBHhsp70 is known to induce the production of RANTES, MIP-1α and MIP-1β. In turn these chemokines should stimulate chemotactic activity.
3) Self-assembly. Refolded m/wAvidin-Linker-N-MTBhsp70 proteins bind biotin. To demonstrate self-assembly, the ability of these proteins to form a stable complex with biotinylated molecules may be demonstrated. Binding to biotinylated Ovalbumin and biotinylated eGFP may be demonstrated. Successful assembly is assessed by immunoprecipitation with anti-MTBhsp70 and anti-biotinylated antigen.
4) In vivo induction of immunity. The immunostimulatory activity of the self-assembled vaccines may be demonstrated by measuring the activation of CD8 T-cells upon immunization of C57BL/6 mice with biotinylated Ovalbumin-m/wAvidin-Linker-N-MTBhsp70 and biotinylated $Ova_{257-264}$-m/wAvidin-Linker-N-MTBhsp70.

Example 3

An MTBHSP70 Construct with Avidin Self Assembled with Biotinylated HRP and Biotinylated Anti-OVA Antibodies Methods i) Plasmid Constructs MTBHSP70 was subcloned into the expression vector pET45b(+) and then linked the CD8 specific Ovalbumin peptide$_{(Ova257-264)}$ at the N-terminal. Avidin and monomeric avidin based on published sequences was assembled and linked at the N-terminal of MTBHSP70 into the expression vector pET45b(+).

ii) Protein Expression and Purification

*E. coli* BL21(DE3) was transformed with the various constructs and expression was induced by addition of IPTG. Proteins were purified by IMAC in the presence of TritonX-114 (Sigma) to remove endotoxins.

iii) Immunizations

C57BL/6 male mice were immunized with Ovalbumin or the $Ova_{257-264}$-L-MTBHSP70 subcutaneously and sacrificed at day 30.

iv) Outcome Measures a. Interferon-γ. After 2 subcutaneous immunizations, mice were sacrificed at day 30 and splenocytes prepared. Splenocytes (2×106 per well) were incubated at 37° C. for 4 hours in presence of brefeldin A (golgi plug) and $Ova_{257-264}$ peptide or an irrelevant peptide. The incubation was stopped by washing cells with 5% FBS in PBS followed by staining for CD3, CD4, CD8 and Interferon-γ after cells were permeabilized with BD's Cytofix/Cytoperm solution. Cell staining was evaluated by flow cytometry and analyzed using FlowJo.
b. Pentamer staining. Cells were treated as described above with the addition that they were initially treated with R-PE conjugated recombinant murine MHC Pentamer H-2Kb SIINFEKL (SEQ ID NO: 4)(from PROIMMUNE).
c. Self-Assembly. An ELISA based assay was employed. Various concentrations of biotinylated Horse Radish Peroxidase (HRP) and purified and refolded avidin-MTBHSP 70 were mixed. The mixture was added to His-Grab plates (ThermoScientific) and unbound biotinylated HRP removed by washing with PBS 0.1% Tween 20 followed by addition of TMB. The reaction was stopped after 20 minutes and the results read at 450 nm.

Results

6×His-MTBHSP 70 ("6×His" disclosed as SEQ ID NO:5) and 6×His-Ova(257-264)-MTBHSP 70 fusion proteins ("6×His" disclosed as SEQ ID NO:5) were expressed in *E. coli* BL21(DE3) cells. In each case, NotI-XhoI MTBHsp70 fragments were used in the fusion constructs. Protein expression was induced by addition of IPTG. Cells were lysed and fractionated into soluble (#1 and #4), periplasmic (#2 and #5) and inclusion body fractions. Aliquots from each fractions were subjected to denaturing SDS-PAGE on 4-12% Bis-Tris NUPAGE gels (Invitrogen).

i) Expression of Avidin and Monomeric Avidin Linked to MTBHSP70 in *E. coli*

Wild-type Avidin (wAvidin) and monomeric Avidin were assembled and cloned into pET45b(+). Fusion constructs were prepared consisting of 6×His-Avidin ("6×His" disclosed as SEQ ID NO:5) linked at the N-terminal of MTBHSP 70. Each plasmid construct was used to transform *E. coli* BL21(DE3) and expression induced with IPTG.

ii) Immunization #1

C57BL/6 male mice were immunized subcutaneously on days 1 and 17 and sacrificed on Day 30 as follows:
Ovalbumin+CFA
Ovalbumin
Ovalbumin+MTBhsp70
Ova$_{peptide}$-MTBhsp70 iii) Outcome Measure

Figure 16:
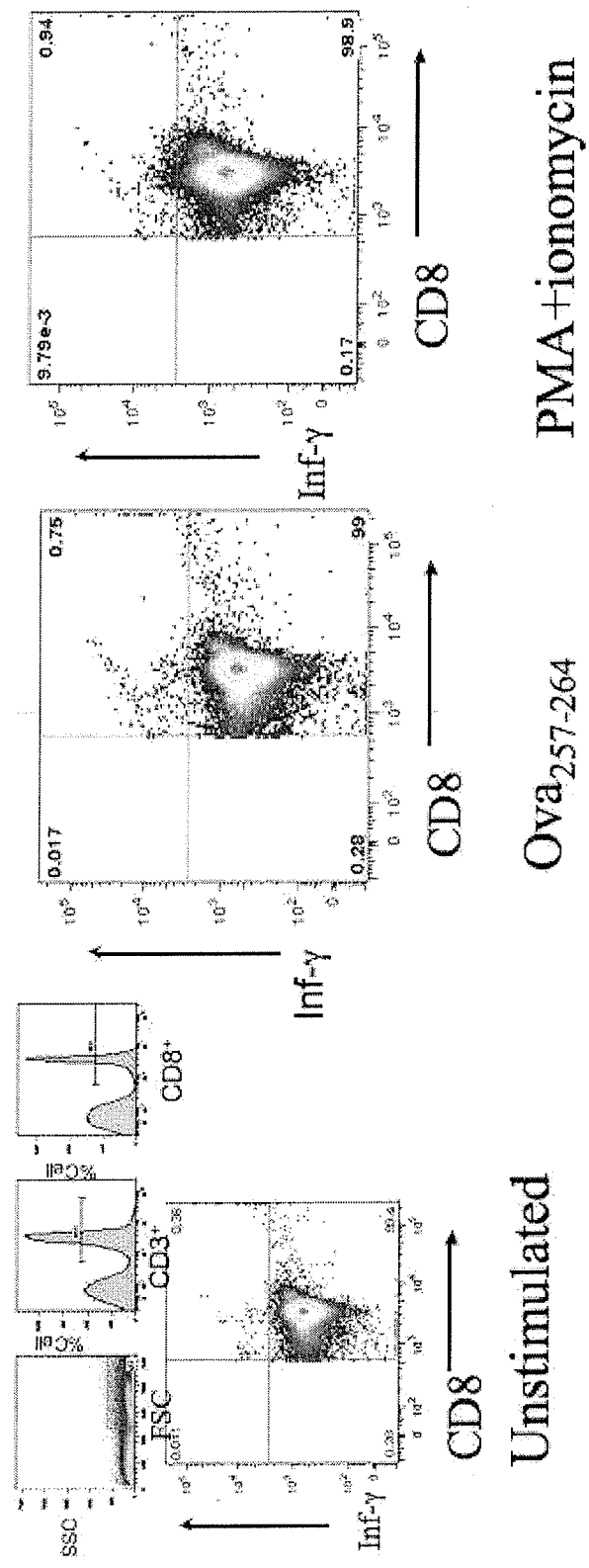
FIG. 16 shows a flow cytometric analysis of interferon-γ production.
Figure 17:
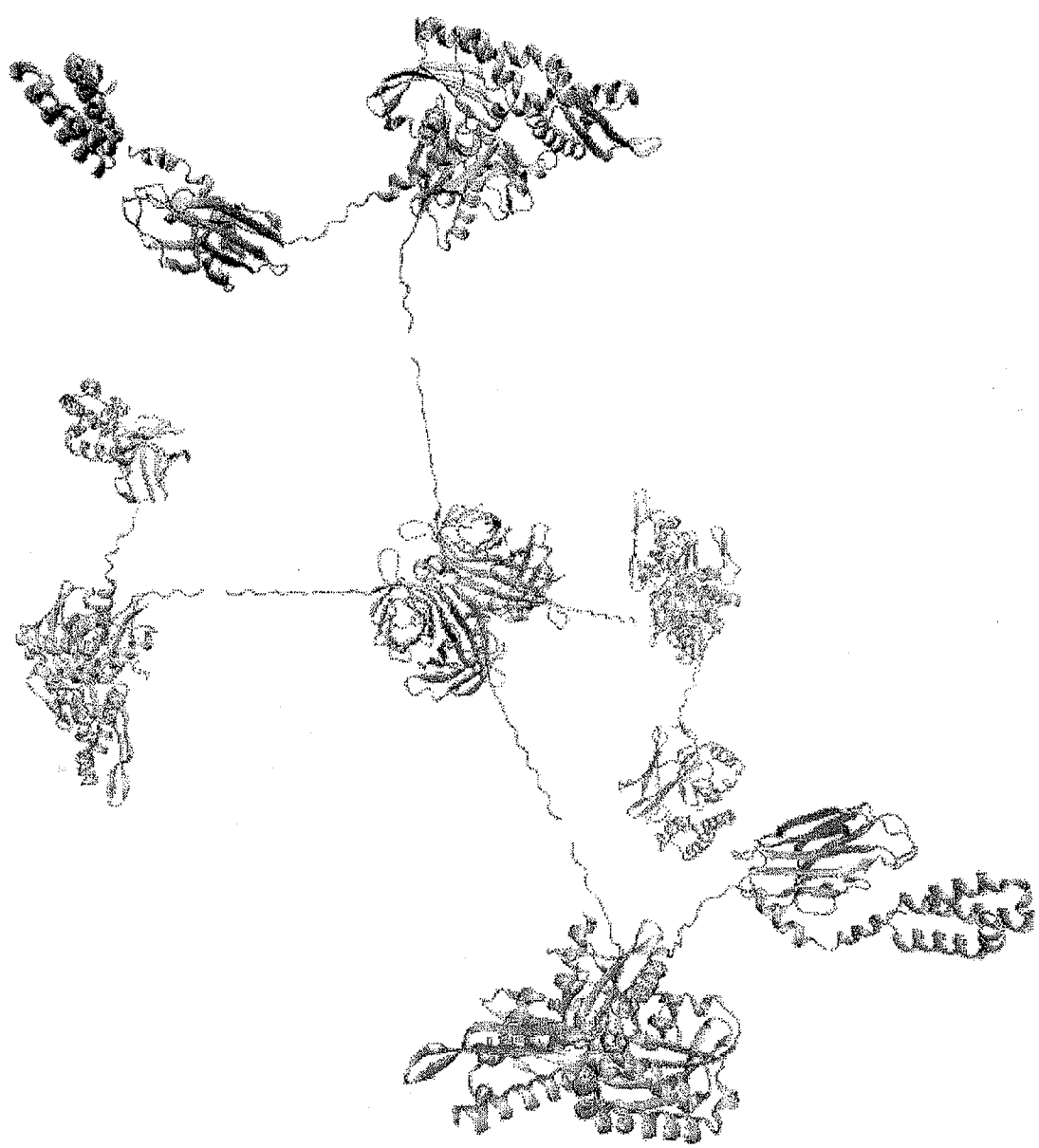
FIG. 17 shows a 2-D molecular model of an MTb HSP70-Avidin fusion with 4 bound monomeric HSP-avidin fusions assembled as a tetramer around 4 tetramerized avidin members, as it assembles to bind biotin.

Production of Interferon gamma upon stimulation of splenocytes with CD8 peptide SIINFEKL (SEQ ID NO: 4) (Ova$_{257-264}$) was measured, and the results are shown in FIG. 16 and Table 1 below.

TABLE 1

Percent CD + 8 splenocytes producing Interferon-γ upon stimulation with Ova$_{257-264}$

| | Percent CD8$^+$Ifnγ$^+$ (minus unstimulated) |
|---|---|
| CFA | 0.39 |
| Ovalbumin | 0.09 |
| Ovalbumin + MTBhsp70 | 0.23 |
| Ovapeptide – MTBhsp70 | 0.22 | iv) Immunization #2

C57BL/6 mice (males) were immunized subcutaneously as described for immunization #1. The immunization groups were as follows:
Group A CFA+Ovalbumin (3 mice)
Group B CFA+Ovapeptide (257-264) (3 mice)
Group C Ovapeptide-MTBhsp70 fusion (3 mice)
Group D Ovapeptide+MTBhsp70 (3 mice)
Group E MTBhsp70 (3 mice)
Group F saline 1 mouse v) Outcome Measure Splenocytes were harvested and stained with CD3, CD4, CD8 and H-2Kb/SIINFEKL (SEQ ID NO: 4) (OVA) Pentamer from ProImmune.

vi) Conclusion

HSP fusion protein constructs were developed and expressed in *E. coli*. Fusion of Ovapeptide 257-264 to the N-terminal of MTBHSP 70 resulted in successful expansion of antigen specific T-cells as measured by Interferon-γ production and H-2Kb/SIINFEKL (SEQ ID NO: 4) (OVA) staining.

Example 4

Modified Constructs to Include Avidin at the N- or C-Terminal of MTBHSP 70 i) Measuring Self-Assembly

Self-assembly of the fusion protein Avidin-MTBHSP 70 with biotinylated horseradish peroxidase (HRP) was assessed using His-Grab plate ELISA. Inclusion bodies were solubilized with guanidium chloride and slowly dialyzed against buffer containing decreasing concentrations of guanidium. The partially refolded protein was incubated with differing amounts of biotinylated HRP prior to being added to a His-Grab plate. The plate was read at 450 nm.

ii) Assessing Targeting of Self-Assembled Vaccine

Targeting of self-assembled vaccine was assessed by flow cytometry. The partially refolded Avidin MTBHSP 70 protein was incubated with biotinylated anti-Ovalbumin antibodies and the complex captured on magnetic His-tag specific beads. After removal of excess antibodies, Alexa Fluor 555 labeled Ovalbumin was added. Samples were analyzed by flow cytometry in the R-PE channel. A very weak difference was observed when compared with beads alone. Targeted self-assembly was confirmed by statistical analyses.

iii) Conclusion

Fusion proteins consisting of either peptide antigens or avidin at the N-term of MTBHSP 70 have been successfully expressed. Immunization with Ovapeptide (257-264) fused in frame at the N-terminal of MTBHSP 70 led to the induction of an antigen specific immune response as measured by Interferon gamma production and the expansion of CD8+ T-cells (pentamer staining) Constructs expressing avidin at the N- or C-terminal of MTBHSP 70 were also designed, thus allowing self assembly of this construct with biotinylated clinically relevant antibodies. The avidin fusion proteins were successfully expressed in *E. coli* but were found in inclusion bodies. Refolding of these proteins was partially successful and is currently being optimized. Low efficiency self assembly of MTBHSP70-avidin with biotinylated monoclonal antibody was demonstrated in preliminary experiments.

References

Chen, W., U. Syldath, et al. (1999). "Human 60-kDa heat-shock protein: a danger signal to the innate immune system." *J Immunol* 162(6): 3212-9.

Laitinen, O. H., H. R. Nordlund, et al. (2007). "Brave new (strept)avidins in biotechnology." *Trends Biotechnol* 25(6): 269-77.

Nordlund, H. R., V. P. Hytonen, et al. (2005). "Tetravalent single-chain avidin: from subunits to protein domains via circularly permuted avidins." *Biochem J* 392(Pt 3): 485-91.

Srivastava, P. K. and R. G. Maki (1991). "Stress-induced proteins in immune response to cancer." *Curr Top Microbiol Immunol* 167: 109-23.

Zugel, U. and S. H. Kaufmann (1999). "Role of heat shock proteins in protection from and pathogenesis of infectious diseases." *Clin Microbiol Rev* 12(1): 19-39.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

REFERENCES

Related approaches are disclosed in PCT/US2007/061554 by the present inventors, of which the entire contents are incorporated herein by reference. Incorporated by reference in their entirety also are any polynucleotide and protein sequences which reference an accession number correlating to an entry in the public database of the National Center for Biotechnology Information (NCBI) on the world wide web at ncbi.nlm.nih.gov. The contents of all cited references including literature references, issued patents, published or non published patent applications as cited throughout this application are also hereby expressly incorporated by reference.

The invention claimed is:

1. A pharmaceutical composition comprising: a pharmaceutically acceptable carrier and a heat shock protein fused to a biotin-binding protein, wherein the biotin-binding protein is non-covalently bound to a biotinylated engineered antibody, the biotinylated engineered antibody is a biotin-containing recombinant molecule that comprises at least an antibody fragment, and the antibody fragment comprises an antigen binding site.

2. The pharmaceutical composition of claim 1, wherein the biotin-binding protein is selected from the group consisting of avidin, streptavidin, and neutravidin.

3. The pharmaceutical composition of claim 1, wherein the heat shock protein is a mammalian heat shock protein or a bacterial heat shock protein.

4. The pharmaceutical composition of claim 1, wherein the heat shock protein is selected from the group consisting of an MTBhsp70 heat shock protein and a human heat shock protein.

5. The pharmaceutical composition of claim 1, which is a vaccine.

6. A method for producing a self-assembling pharmaceutical composition of claim 1, comprising contacting a heat shock protein fused to a biotin-binding protein, wherein the biotin-binding protein is non-covalently bound to a biotinylated engineered antibody, sufficient to form a non-covalent complex of the heat shock protein and the biotinylated engineered antibody, the biotinylated engineered antibody is a biotin-containing recombinant molecule that comprises at least an antibody fragment, and the antibody fragment comprises an antigen binding site.

7. The pharmaceutical composition of claim 1, wherein the biotinylated engineered antibody comprises a scFv fragment.

8. The pharmaceutical composition of claim 1, wherein the biotinylated engineered antibody comprises a Fab fragment.

9. The pharmaceutical composition of claim 1, wherein the biotinylated engineered antibody is multivalent.

10. The pharmaceutical composition of claim 1, wherein the biotinylated engineered antibody is tetravalent.

11. A method for inducing an immune response in a subject, comprising administering to the subject a pharmaceutical composition comprising a pharmaceutically acceptable carrier and a heat shock protein fused to a biotin-binding protein, wherein the biotin-binding protein is non-covalently bound to a biotinylated engineered antibody, the biotinylated engineered antibody is a biotin-containing recombinant molecule that comprises at least an antibody fragment, and the antibody fragment comprises an antigen binding site.

12. The method of claim 11, wherein the biotin-binding protein is selected from the group consisting of avidin, streptavidin, and neutravidin.

13. The method of claim 11, wherein the heat shock protein is a mammalian heat shock protein or a bacterial heat shock protein.

14. The method of claim 11, wherein the heat shock protein is selected from the group consisting of an MTBhsp70 heat shock protein and a human heat shock protein.

15. The method of claim 11, wherein the pharmaceutical composition is administered to the subject as a non-covalent complex.

* * * * *

SEQUENCE LISTING

<160> NUMBER OF SEQ ID NOS: 24

<210> SEQ ID NO 1
<211> LENGTH: 625
<212> TYPE: PRT
<213> ORGANISM: Mycobacterium tuberculosis

<400> SEQUENCE: 1

```
Met Ala Arg Ala Val Gly Ile Asp Leu Gly Thr Thr Asn Ser Val Val
1               5                   10                  15

Ser Val Le

```
Thr Pro Leu Ser Leu Gly Ile Glu Thr Lys Gly Gly Val Met Thr Arg
        370             375             380

Leu Ile Glu Arg Asn Thr Thr Ile Pro Thr Lys Arg Ser Glu Thr Phe
385             390             395             400

Thr Thr Ala Asp Asp Asn Gln Pro Ser Val Gln Ile Gln Val Tyr Gln
            405             410             415

Gly Glu Arg Glu Ile Ala Ala His Asn Lys Leu Leu Gly Ser Phe Glu
        420             425             430

Leu Thr Gly Ile Pro Pro Ala Pro Arg Gly Ile Pro Gln Ile Glu Val
            435             440             445

Thr Phe Asp Ile Asp Ala Asn Gly Ile Val His Val Thr Ala Lys Asp
450             455             460

Lys Gly Thr Gly Lys Glu Asn Thr Ile Arg Ile Gln Glu Gly Ser Gly
465             470             475             480

Leu Ser Lys Glu Asp Ile Asp Arg Met Ile Lys Asp Ala Glu Ala His
            485             490             495

Ala Glu Glu Asp Arg Lys Arg Glu Glu Ala Asp Val Arg Asn Gln
        500             505             510

Ala Glu Thr Leu Val Tyr Gln Thr Glu Lys Phe Val Lys Glu Gln Arg
    515             520             525

Glu Ala Glu Gly Gly Ser Lys Val Pro Glu Asp Thr Leu Asn Lys Val
530             535             540

Asp Ala Ala Val Ala Glu Ala Lys Ala Ala Leu Gly Gly Ser Asp Ile
545             550             555             560

Ser Ala Ile Lys Ser Ala Met Glu Lys Leu Gly Gln Glu Ser Gln Ala
            565             570             575

Leu Gly Gln Ala Ile Tyr Glu Ala Ala Gln Ala Ala Ser Gln Ala Thr
        580             585             590

Gly Ala Ala His Pro Gly Gly Glu Pro Gly Gly Ala His Pro Gly Ser
            595             600             605

Ala Asp Asp Val Val Asp Ala Glu Val Val Asp Gly Arg Glu Ala
    610             615             620

Lys
625

<210> SEQ ID NO 2
<211> LENGTH: 625
<212> TYPE: PRT
<213> ORGANISM: Mycobacterium bovis

<400> SEQUENCE: 2

Met Ala Arg Ala Val Gly Ile Asp Leu Gly Thr Thr Asn Ser Val Val
1               5                   10                  15

Ser Val Leu Glu Gly Gly Asp Pro Val Val Ala Asn Ser Glu Gly
            20              25                  30

Ser Arg Thr Thr Pro Ser Ile Val Ala Phe Ala Arg Asn Gly Glu Val
            35              40                  45

Leu Val Gly Gln Pro Ala Lys Asn Gln Ala Val Thr Asn Val Asp Arg
50              55                  60

Thr Val Arg Ser Val Lys Arg His Met Gly Ser Asp Trp Ser Ile Glu
65              70                  75                  80

Ile Asp Gly Lys Lys Tyr Thr Ala Pro Glu Ile Ser Ala Arg Ile Leu
            85                  90                  95

Met Lys Leu Lys Arg Asp Ala Glu Ala Tyr Leu Gly Glu Asp Ile Thr
            100                 105                 110
```

```
Asp Ala Val Ile Thr Thr Pro Ala Tyr Phe Asn Asp Ala Gln Arg Gln
            115                 120                 125

Ala Thr Lys Asp Ala Gly Gln Ile Ala Gly Leu Asn Val Leu Arg Ile
130                 135                 140

Val Asn Glu Pro Thr Ala Ala Leu Ala Tyr Gly Leu Asp Lys Gly
145                 150                 155                 160

Glu Lys Glu Gln Arg Ile Leu Val Phe Asp Leu Gly Gly Gly Thr Phe
                165                 170                 175

Asp Val Ser Leu Leu Glu Ile Gly Glu Gly Val Val Glu Val Arg Ala
            180                 185                 190

Thr Ser Gly Asp Asn His Leu Gly Gly Asp Asp Trp Asp Gln Arg Val
            195                 200                 205

Val Asp Trp Leu Val Asp Lys Phe Lys Gly Thr Ser Gly Ile Asp Leu
        210                 215                 220

Thr Lys Asp Lys Met Ala Met Gln Arg Leu Arg Glu Ala Ala Glu Lys
225                 230                 235                 240

Ala Lys Ile Glu Leu Ser Ser Ser Gln Ser Thr Ser Ile Asn Leu Pro
                245                 250                 255

Tyr Ile Thr Val Asp Ala Asp Lys Asn Pro Leu Phe Leu Asp Glu Gln
                260                 265                 270

Leu Thr Arg Ala Glu Phe Gln Arg Ile Thr Gln Asp Leu Leu Asp Arg
            275                 280                 285

Thr Arg Lys Pro Phe Gln Ser Val Ile Ala Asp Thr Gly Ile Ser Val
        290                 295                 300

Ser Glu Ile Asp His Val Leu Val Gly Gly Ser Thr Arg Met Pro
305                 310                 315                 320

Ala Val Thr Asp Leu Val Lys Glu Leu Thr Gly Gly Lys Glu Pro Asn
                325                 330                 335

Lys Gly Val Asn Pro Asp Glu Val Val Ala Val Gly Ala Ala Leu Gln
                340                 345                 350

Ala Gly Val Leu Lys Gly Glu Val Lys Asp Val Leu Leu Leu Asp Val
            355                 360                 365

Thr Pro Leu Ser Leu Gly Ile Glu Thr Lys Gly Gly Val Met Thr Arg
        370                 375                 380

Leu Ile Glu Arg Asn Thr Thr Ile Pro Thr Lys Arg Ser Glu Thr Phe
385                 390                 395                 400

Thr Thr Ala Asp Asp Asn Gln Pro Ser Val Gln Ile Gln Val Tyr Gln
                405                 410                 415

Gly Glu Arg Glu Ile Ala Ala His Asn Lys Leu Leu Gly Ser Phe Glu
                420                 425                 430

Leu Thr Gly Ile Pro Pro Ala Pro Arg Gly Ile Pro Gln Ile Glu Val
            435                 440                 445

Thr Phe Asp Ile Asp Ala Asn Gly Ile Val His Val Thr Ala Lys Asp
        450                 455                 460

Lys Gly Thr Gly Lys Glu Asn Thr Ile Arg Ile Gln Glu Gly Ser Gly
465                 470                 475                 480

Leu Ser Lys Glu Asp Ile Asp Arg Met Ile Lys Asp Ala Glu Ala His
                485                 490                 495

Ala Glu Glu Asp Arg Lys Arg Arg Glu Glu Ala Asp Val Arg Asn Gln
                500                 505                 510

Ala Glu Thr Leu Val Tyr Gln Thr Glu Lys Phe Val Lys Glu Gln Arg
            515                 520                 525
```

```
Glu Ala Glu Gly Gly Ser Lys Val Pro Glu Asp Thr Leu Asn Lys Val
    530                 535                 540

Asp Ala Ala Val Ala Glu Ala Lys Ala Ala Leu Gly Gly Ser Asp Ile
545                 550                 555                 560

Ser Ala Ile Lys Ser Ala Met Glu Lys Leu Gly Gln Glu Ser Gln Ala
                565                 570                 575

Leu Gly Gln Ala Ile Tyr Glu Ala Ala Gln Ala Ala Ser Gln Ala Thr
            580                 585                 590

Gly Ala Ala His Pro Gly Gly Glu Pro Gly Gly Ala His Pro Gly Ser
                595                 600                 605

Ala Asp Asp Val Val Asp Ala Glu Val Val Asp Asp Gly Arg Glu Ala
            610                 615                 620

Lys
625

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Asp Glu Leu
1

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ile Ile Asn Phe Glu Lys Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (157)..(351)

<400> SEQUENCE: 6
tggcgccggt gatgccggcc acgatgcgtc cggcgtagag gatcgagatc gatctcgatc     60
```

```
ccgcgaaatt aatacgactc actatagggg aattgtgagc ggataacaat tcccctctag      120
aaataatttt gtttaacttt aagaaggaga tatacc atg gca cat cac cac cac        174
                                       Met Ala His His His His
                                        1               5 cat cac gtg ggt acc ggt tcg aat gat gac gac gac aag agt ccg gat        222
His His Val Gly Thr Gly Ser Asn Asp Asp Asp Asp Lys Ser Pro Asp
            10                  15                  20 ccc aat tgg gag ctc gtg tac acg gcg cgc ctg cag gtc gac aag ctt        270
Pro Asn Trp Glu Leu Val Tyr Thr Ala Arg Leu Gln Val Asp Lys Leu
        25                  30                  35 gcg gcc gca ctc gag tct ggt aaa gaa acc gct gct gcg aaa ttt gaa        318
Ala Ala Ala Leu Glu Ser Gly Lys Glu Thr Ala Ala Ala Lys Phe Glu
40                  45                  50 cgc cag cac atg gac tcg tct act agc gca gct taattaacct aggctgctgc     371
Arg Gln His Met Asp Ser Ser Thr Ser Ala Ala
55                  60                  65 caccgctgag caataactag cataa                                            396

<210> SEQ ID NO 7
<211> LENGTH: 65
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala His His His His His Val Gly Thr Gly Ser Asn Asp Asp
1               5                   10                  15

Asp Asp Lys Ser Pro Asp Pro Asn Trp Glu Leu Val Tyr Thr Ala Arg
                20                  25                  30

Leu Gln Val Asp Lys Leu Ala Ala Ala Leu Glu Ser Gly Lys Glu Thr
            35                  40                  45

Ala Ala Ala Lys Phe Glu Arg Gln His Met Asp Ser Ser Thr Ser Ala
        50                  55                  60

Ala
65

<210> SEQ ID NO 8
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala His His His His His Val Gly Thr Gly Ser Asn Asp Asp
1               5                   10                  15

Asp Asp Lys Ser Pro Ala Gln Leu Ser Ile Ile Asn Phe Glu Lys Leu
                20                  25                  30

Ala Ala Ala Met Ala Arg Ala Val Gly Ile Asp Leu Gly Thr Thr Asn
            35                  40                  45

Ser Val Val Ser Val Leu Glu Gly Gly Asp Pro Val Val Val Ala Asn
        50                  55                  60

Ser Glu Gly Ser Arg Thr Thr Pro Ser Ile Val Ala Phe Ala Arg Asn
65                  70                  75                  80

Gly Glu Val Leu Val Gly Gln Pro Ala Lys Asn Gln Ala Val Thr Asn
                85                  90                  95
```

```
Val Asp Arg Thr Val Arg Ser Val Lys Arg His Met Gly Ser Asp Trp
            100                 105                 110
Ser Ile Glu Ile Asp Gly Lys Lys Tyr Thr Ala Pro Glu Ile Ser Ala
        115                 120                 125
Arg Ile Leu Met Lys Leu Lys Arg Asp Ala Glu Ala Tyr Leu Gly Glu
    130                 135                 140
Asp Ile Thr Asp Ala Val Ile Thr Thr Pro Ala Tyr Phe Asn Asp Ala
145                 150                 155                 160
```

<210> SEQ ID NO 9
<211> LENGTH: 378
<212> TYPE: DNA
<213> ORGANISM: Unknown
<220> FEATURE:
<223> OTHER INFORMATION: Description of Unknown: Monomeric avidin polynucleotide
<220> FEATURE:
<221> NAME/KEY: CDS
<222> LOCATION: (1)..(375)

<400> SEQUENCE: 9

```
atg gcg cgt aaa tgc agc ctg acc ggc aaa tgg acc aac gat ctg ggc    48
Met Ala Arg Lys Cys Ser Leu Thr Gly Lys Trp Thr Asn Asp Leu Gly
1               5                   10                  15 tcc aac atg acc atc ggg gct gtg aac agc aga ggt gaa ttc aca ggc    96
Ser Asn Met Thr Ile Gly Ala Val Asn Ser Arg Gly Glu Phe Thr Gly
            20                  25                  30 acc tac atc aca gcc gta aca gcc aca tca aat gag atc aaa gag tca   144
Thr Tyr Ile Thr Ala Val Thr Ala Thr Ser Asn Glu Ile Lys Glu Ser
        35                  40                  45 cca ctg cat ggg aca caa gcc acc atc aac aag agg acc cag ccc acc   192
Pro Leu His Gly Thr Gln Ala Thr Ile Asn Lys Arg Thr Gln Pro Thr
    50                  55                  60 ttt ggc ttc acc gtc gct tgg aag ttt tca gag tcc acc act gtc ttc   240
Phe Gly Phe Thr Val Ala Trp Lys Phe Ser Glu Ser Thr Thr Val Phe
65                  70                  75                  80 acg ggc cag tgc ttc ata gac agg aat ggg aag gag gtc ctg aag acc   288
Thr Gly Gln Cys Phe Ile Asp Arg Asn Gly Lys Glu Val Leu Lys Thr
                85                  90                  95 gcg tgg ctg ctg cgg tca agt gtt aat gac att ggt gat gac tgg aaa   336
Ala Trp Leu Leu Arg Ser Ser Val Asn Asp Ile Gly Asp Asp Trp Lys
            100                 105                 110 gct acc agg gcc ggc atc aac gcc ttc act cgc ctg cag tga            378
Ala Thr Arg Ala Gly Ile Asn Ala Phe Thr Arg Leu Gln
        115                 120                 125
```

<210> SEQ ID NO 10
<211> LENGTH: 125
<212> TYPE: PRT
<213> ORGANISM: Unknown
<220> FEATURE:
<223> OTHER INFORMATION: Description of Unknown: Monomeric avidin polypeptide

<400> SEQUENCE: 10

```
Met Ala Arg Lys Cys Ser Leu Thr Gly Lys Trp Thr Asn Asp Leu Gly
1               5                   10                  15

Ser Asn Met Thr Ile Gly Ala Val Asn Ser Arg Gly Glu Phe Thr Gly
            20                  25                  30

Thr Tyr Ile Thr Ala Val Thr Ala Thr Ser Asn Glu Ile Lys Glu Ser
        35                  40                  45

Pro Leu His Gly Thr Gln Ala Thr Ile Asn Lys Arg Thr Gln Pro Thr
```

```
                    50                  55                  60
Phe Gly Phe Thr Val Ala Trp Lys Phe Ser Glu Ser Thr Thr Val Phe
 65                  70                  75                  80

Thr Gly Gln Cys Phe Ile Asp Arg Asn Gly Lys Glu Val Leu Lys Thr
                 85                  90                  95

Ala Trp Leu Leu Arg Ser Ser Val Asn Asp Ile Gly Asp Asp Trp Lys
            100                 105                 110

Ala Thr Arg Ala Gly Ile Asn Ala Phe Thr Arg Leu Gln
        115                 120                 125

<210> SEQ ID NO 11
<211> LENGTH: 378
<212> TYPE: DNA
<213> ORGANISM: Unknown
<220> FEATURE:
<223> OTHER INFORMATION: Description of Unknown: Wild-type avidin
      polynucleotide
<220> FEATURE:
<221> NAME/KEY: CDS
<222> LOCATION: (1)..(375)

<400> SEQUENCE: 11 atg gcg cgt aaa tgc agc ctg acc ggc aaa tgg acc aac gat ctg ggc      48
Met Ala Arg Lys Cys Ser Leu Thr Gly Lys Trp Thr Asn Asp Leu Gly
 1               5                  10                  15 tcc aac atg acc atc ggg gct gtg aac agc aga ggt gaa ttc aca ggc      96
Ser Asn Met Thr Ile Gly Ala Val Asn Ser Arg Gly Glu Phe Thr Gly
             20                  25                  30 acc tac atc aca gcc gta aca gcc aca tca aat gag atc aaa gag tca     144
Thr Tyr Ile Thr Ala Val Thr Ala Thr Ser Asn Glu Ile Lys Glu Ser
         35                  40                  45 cca ctg cat ggg aca caa aac acc atc aac aag agg acc cag ccc acc     192
Pro Leu His Gly Thr Gln Asn Thr Ile Asn Lys Arg Thr Gln Pro Thr
     50                  55                  60 ttt ggc ttc acc gtc aat tgg aag ttt tca gag tcc acc act gtc ttc     240
Phe Gly Phe Thr Val Asn Trp Lys Phe Ser Glu Ser Thr Thr Val Phe
 65                  70                  75                  80 acg ggc cag tgc ttc ata gac agg aat ggg aag gag gtc ctg aag acc     288
Thr Gly Gln Cys Phe Ile Asp Arg Asn Gly Lys Glu Val Leu Lys Thr
                 85                  90                  95 atg tgg ctg ctg cgg tca agt gtt aat gac att ggt gat gac tgg aaa     336
Met Trp Leu Leu Arg Ser Ser Val Asn Asp Ile Gly Asp Asp Trp Lys
            100                 105                 110 gct acc agg gtc ggc atc aac atc ttc act cgc ctg cag tga             378
Ala Thr Arg Val Gly Ile Asn Ile Phe Thr Arg Leu Gln
        115                 120                 125

<210> SEQ ID NO 12
<211> LENGTH: 125
<212> TYPE: PRT
<213> ORGANISM: Unknown
<220> FEATURE:
<223> OTHER INFORMATION: Description of Unknown: Wild-type avidin
      polypeptide

<400> SEQUENCE: 12

Met Ala Arg Lys Cys Ser Leu Thr Gly Lys Trp Thr Asn Asp Leu Gly
 1               5                  10                  15

Ser Asn Met Thr Ile Gly Ala Val Asn Ser Arg Gly Glu Phe Thr Gly
             20                  25                  30

Thr Tyr Ile Thr Ala Val Thr Ala Thr Ser Asn Glu Ile Lys Glu Ser
         35                  40                  45
```

```
Pro Leu His Gly Thr Gln Asn Thr Ile Asn Lys Arg Thr Gln Pro Thr
    50                  55                  60

Phe Gly Phe Thr Val Asn Trp Lys Phe Ser Glu Ser Thr Thr Val Phe
65                  70                  75                  80

Thr Gly Gln Cys Phe Ile Asp Arg Asn Gly Lys Glu Val Leu Lys Thr
                85                  90                  95

Met Trp Leu Leu Arg Ser Ser Val Asn Asp Ile Gly Asp Asp Trp Lys
                100                 105                 110

Ala Thr Arg Val Gly Ile Asn Ile Phe Thr Arg Leu Gln
                115                 120                 125

<210> SEQ ID NO 13
<211> LENGTH: 407
<212> TYPE: DNA
<213> ORGANISM: Artificial Sequence
<220> FEATURE:
<223> OTHER INFORMATION: Description of Artificial Sequence: Synthetic
      intentionally erroneous polynucleotide
<220> FEATURE:
<221> NAME/KEY: CDS
<222> LOCATION: (1)..(291)
<220> FEATURE:
<221> NAME/KEY: CDS
<222> LOCATION: (295)..(312)
<220> FEATURE:
<221> NAME/KEY: CDS
<222> LOCATION: (316)..(405)

<400> SEQUENCE: 13 agt ccg gcc cag ccg gcc atg gcg cgt aaa tgc agc ctg acc ggc aaa        48
Ser Pro Ala Gln Pro Ala Met Ala Arg Lys Cys Ser Leu Thr Gly Lys
1               5                   10                  15 tgg acc aac gat ctg ggc tcc aac atg acc atc ggg gct gtg aac agc        96
Trp Thr Asn Asp Leu Gly Ser Asn Met Thr Ile Gly Ala Val Asn Ser
                20                  25                  30 aga ggt gaa ttc aca ggc acc tac atc aca gcc gta aca gcc aca tca       144
Arg Gly Glu Phe Thr Gly Thr Tyr Ile Thr Ala Val Thr Ala Thr Ser
            35                  40                  45 aat gag atc aaa gag tca cca ctg cat ggg aca caa gcc acc atc aac       192
Asn Glu Ile Lys Glu Ser Pro Leu His Gly Thr Gln Ala Thr Ile Asn
50                  55                  60 aag agg atc cag ccc acc ttt ggc ttc acc gtc gct tgg aag ttt tca       240
Lys Arg Ile Gln Pro Thr Phe Gly Phe Thr Val Ala Trp Lys Phe Ser
65                  70                  75                  80 gag tcc acc act gtc ttc acg ggc cag tgc ttc ata gac agg aat gga       288
Glu Ser Thr Thr Val Phe Thr Gly Gln Cys Phe Ile Asp Arg Asn Gly
                85                  90                  95 ctc tga aaa ctt cca agg agg tcc tga aga ccg cgt ggc tgc tgc ggt       336
Leu     Lys Leu Pro Arg Arg Ser     Arg Pro Arg Gly Cys Cys Gly
                100                 105                 110 caa gtg tta atg aca ttg gtg atg act gga aag cta cca ggg ccg gcg       384
Gln Val Leu Met Thr Leu Val Met Thr Gly Lys Leu Pro Gly Pro Ala
                115                 120                 125 cca aca tct tca ctc gcc tgc ag                                        407
Pro Thr Ser Ser Leu Ala Cys
    130

<210> SEQ ID NO 14
<211> LENGTH: 97
<212> TYPE: PRT
<213> ORGANISM: Artificial Sequence
<220> FEATURE:
<223> OTHER INFORMATION: Description of Artificial Sequence: Synthetic
``` intentionally erroneous polypeptide

<400> SEQUENCE: 14

Ser Pro Ala Gln Pro Ala Met Ala Arg Lys Cys Ser Leu Thr Gly Lys
1               5                   10                  15

Trp Thr Asn Asp Leu Gly Ser Asn Met Thr Ile Gly Ala Val Asn Ser
            20                  25                  30

Arg Gly Glu Phe Thr Gly Thr Tyr Ile Thr Ala Val Thr Ala Thr Ser
        35                  40                  45

Asn Glu Ile Lys Glu Ser Pro Leu His Gly Thr Gln Ala Thr Ile Asn
    50                  55                  60

Lys Arg Ile Gln Pro Thr Phe Gly Phe Thr Val Ala Trp Lys Phe Ser
65                  70                  75                  80

Glu Ser Thr Thr Val Phe Thr Gly Gln Cys Phe Ile Asp Arg Asn Gly
                85                  90                  95

Leu

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      intentionally erroneous peptide

<400> SEQUENCE: 15

Lys Leu Pro Arg Arg Ser
1               5

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      intentionally erroneous polypeptide

<400> SEQUENCE: 16

Arg Pro Arg Gly Cys Cys Gly Gln Val Leu Met Thr Leu Val Met Thr
1               5                   10                  15

Gly Lys Leu Pro Gly Pro Ala Pro Thr Ser Ser Leu Ala Cys
            20                  25                  30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caagaggacc cagcccacct ttggc                                        25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

```
tgggctgggt cctcttgttg atggt                                        25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aggaatggga aggaggtcct gaaga                                        25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggacctcctt cccattcctg tctat                                        25

<210> SEQ ID NO 21
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(600)

<400> SEQUENCE: 21 atg gca cat cac cac cac cat cac gtg ggt acc ggt tcg aat gat gac      48
Met Ala His His His His His His Val Gly Thr Gly Ser Asn Asp Asp
1               5                   10                  15 gac gac aag agt ccg gcc cag ccg gcc atg gcg cgt aaa tgc agc ctg      96
Asp Asp Lys Ser Pro Ala Gln Pro Ala Met Ala Arg Lys Cys Ser Leu
            20                  25                  30 acc ggc aaa tgg acc aac gat ctg ggc tcc aac atg acc atc ggg gct    144
Thr Gly Lys Trp Thr Asn Asp Leu Gly Ser Asn Met Thr Ile Gly Ala
        35                  40                  45 gtg aac agc aga ggt gaa ttc aca ggc acc tac atc aca gcc gta aca    192
Val Asn Ser Arg Gly Glu Phe Thr Gly Thr Tyr Ile Thr Ala Val Thr
    50                  55                  60 gcc aca tca aat gag atc aaa gag tca cca ctg cat ggg aca caa gcc    240
Ala Thr Ser Asn Glu Ile Lys Glu Ser Pro Leu His Gly Thr Gln Ala
65                  70                  75                  80 acc atc aac aag agg acc cag ccc acc ttt ggc ttc acc gtc gct tgg    288
Thr Ile Asn Lys Arg Thr Gln Pro Thr Phe Gly Phe Thr Val Ala Trp
                85                  90                  95 aag ttt tca gag tcc acc act gtc ttc acg ggc cag tgc ttc ata gac    336
Lys Phe Ser Glu Ser Thr Thr Val Phe Thr Gly Gln Cys Phe Ile Asp
            100                 105                 110 agg aat ggg aag gag gtc ctg aag acc gcg tgg ctg ctg cgg tca agt    384
Arg Asn Gly Lys Glu Val Leu Lys Thr Ala Trp Leu Leu Arg Ser Ser
        115                 120                 125 gtt aat gac att ggt gat gac tgg aaa gct acc agg gcc ggc gcc aac    432
Val Asn Asp Ile Gly Asp Asp Trp Lys Ala Thr Arg Ala Gly Ala Asn
    130                 135                 140 atc ttc act cgc ctg cag ggt gga ggc ggt tca ggc gga ggt ggc tct    480
```

```
Ile Phe Thr Arg Leu Gln Gly Gly Gly Ser Gly Gly Gly Gly Ser
145                 150                 155                 160 ggc ggt ggc gga tcg cgg gcg gcc gct atg gct cgt gcg gtg ggg atc    528
Gly Gly Gly Gly Ser Arg Ala Ala Ala Met Ala Arg Ala Val Gly Ile
                165                 170                 175 gac ctc ggg acc acc aac tcc gtc gtc tcg gtt ctg gaa ggt ggc gac    576
Asp Leu Gly Thr Thr Asn Ser Val Val Ser Val Leu Glu Gly Gly Asp
            180                 185                 190 ccg gtc gtc gtc gcc aac tcc gag                                    600
Pro Val Val Val Ala Asn Ser Glu
        195                 200

<210> SEQ ID NO 22
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala His His His His His His Val Gly Thr Gly Ser Asn Asp Asp
1               5                   10                  15

Asp Asp Lys Ser Pro Ala Gln Pro Ala Met Ala Arg Lys Cys Ser Leu
                20                  25                  30

Thr Gly Lys Trp Thr Asn Asp Leu Gly Ser Asn Met Thr Ile Gly Ala
            35                  40                  45

Val Asn Ser Arg Gly Glu Phe Thr Gly Thr Tyr Ile Thr Ala Val Thr
        50                  55                  60

Ala Thr Ser Asn Glu Ile Lys Glu Ser Pro Leu His Gly Thr Gln Ala
65                  70                  75                  80

Thr Ile Asn Lys Arg Thr Gln Pro Thr Phe Gly Phe Thr Val Ala Trp
                85                  90                  95

Lys Phe Ser Glu Ser Thr Thr Val Phe Thr Gly Gln Cys Phe Ile Asp
            100                 105                 110

Arg Asn Gly Lys Glu Val Leu Lys Thr Ala Trp Leu Leu Arg Ser Ser
        115                 120                 125

Val Asn Asp Ile Gly Asp Asp Trp Lys Ala Thr Arg Ala Gly Ala Asn
130                 135                 140

Ile Phe Thr Arg Leu Gln Gly Gly Gly Ser Gly Gly Gly Gly Ser
145                 150                 155                 160

Gly Gly Gly Gly Ser Arg Ala Ala Ala Met Ala Arg Ala Val Gly Ile
                165                 170                 175

Asp Leu Gly Thr Thr Asn Ser Val Val Ser Val Leu Glu Gly Gly Asp
            180                 185                 190

Pro Val Val Val Ala Asn Ser Glu
        195                 200

<210> SEQ ID NO 23
<211> LENGTH: 600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(600)

<400> SEQUENCE: 23
```

```
atg gca cat cac cac cac cat cac gtg ggt acc ggt tcg aat gat gac      48
Met Ala His His His His His His Val Gly Thr Gly Ser Asn Asp Asp
1               5                   10                  15 gac gac aag agt ccg gcc cag ccg gcc atg gcg cgt aaa tgc agc ctg      96
Asp Asp Lys Ser Pro Ala Gln Pro Ala Met Ala Arg Lys Cys Ser Leu
                20                  25                  30 acc ggc aaa tgg acc aac gat ctg ggc tcc aac atg acc atc ggg gct     144
Thr Gly Lys Trp Thr Asn Asp Leu Gly Ser Asn Met Thr Ile Gly Ala
            35                  40                  45 gtg aac agc aga ggt gaa ttc aca ggc acc tac atc aca gcc gta aca     192
Val Asn Ser Arg Gly Glu Phe Thr Gly Thr Tyr Ile Thr Ala Val Thr
50                  55                  60 gcc aca tca aat gag atc aaa gag tca cca ctg cat ggg aca caa aac     240
Ala Thr Ser Asn Glu Ile Lys Glu Ser Pro Leu His Gly Thr Gln Asn
65                  70                  75                  80 acc atc aac aag agg acc cag ccc acc ttt ggc ttc acc gtc aat tgg     288
Thr Ile Asn Lys Arg Thr Gln Pro Thr Phe Gly Phe Thr Val Asn Trp
                85                  90                  95 aag ttt tca gag tcc acc act gtc ttc acg ggc cag tgc ttc ata gac     336
Lys Phe Ser Glu Ser Thr Thr Val Phe Thr Gly Gln Cys Phe Ile Asp
            100                 105                 110 agg aat ggg aag gag gtc ctg aag acc atg tgg ctg ctg cgg tca agt     384
Arg Asn Gly Lys Glu Val Leu Lys Thr Met Trp Leu Leu Arg Ser Ser
        115                 120                 125 gtt aat gac att ggt gat gac tgg aaa gct acc agg gtc ggc atc aac     432
Val Asn Asp Ile Gly Asp Asp Trp Lys Ala Thr Arg Val Gly Ile Asn
130                 135                 140 atc ttc act cgc ctg cag ggt gga ggc ggt tca ggc gga ggt ggc tct     480
Ile Phe Thr Arg Leu Gln Gly Gly Gly Gly Ser Gly Gly Gly Gly Ser
145                 150                 155                 160 ggc ggt ggc gga tcg cgg gcg gcc gct atg gct cgt gcg gtc ggg atc     528
Gly Gly Gly Gly Ser Arg Ala Ala Ala Met Ala Arg Ala Val Gly Ile
                165                 170                 175 gac ctc ggg acc acc aac tcc gtc gtc tcg gtt ctg gaa ggt ggc gac     576
Asp Leu Gly Thr Thr Asn Ser Val Val Ser Val Leu Glu Gly Gly Asp
            180                 185                 190 ccg gtc gtc gtc gcc aac tcc gag                                    600
Pro Val Val Val Ala Asn Ser Glu
        195                 200

<210> SEQ ID NO 24
<211> LENGTH: 200
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala His His His His His His Val Gly Thr Gly Ser Asn Asp Asp
1               5                   10                  15

Asp Asp Lys Ser Pro Ala Gln Pro Ala Met Ala Arg Lys Cys Ser Leu
                20                  25                  30

Thr Gly Lys Trp Thr Asn Asp Leu Gly Ser Asn Met Thr Ile Gly Ala
            35                  40                  45

Val Asn Ser Arg Gly Glu Phe Thr Gly Thr Tyr Ile Thr Ala Val Thr
50                  55                  60

Ala Thr Ser Asn Glu Ile Lys Glu Ser Pro Leu His Gly Thr Gln Asn
65                  70                  75                  80

Thr Ile Asn Lys Arg Thr Gln Pro Thr Phe Gly Phe Thr Val Asn Trp
```

```
                    85                    90                     95
Lys Phe Ser Glu Ser Thr Thr Val Phe Thr Gly Gln Cys Phe Ile Asp
            100                    105                110

Arg Asn Gly Lys Glu Val Leu Lys Thr Met Trp Leu Leu Arg Ser Ser
        115                 120                 125

Val Asn Asp Ile Gly Asp Asp Trp Lys Ala Thr Arg Val Gly Ile Asn
    130                 135                 140

Ile Phe Thr Arg Leu Gln Gly Gly Gly Ser Gly Gly Gly Gly Gly Ser
145             150                 155                 160

Gly Gly Gly Gly Ser Arg Ala Ala Ala Met Ala Arg Ala Val Gly Ile
            165                 170                 175

Asp Leu Gly Thr Thr Asn Ser Val Val Ser Val Leu Glu Gly Gly Asp
            180                 185                 190

Pro Val Val Val Ala Asn Ser Glu
        195                 200
```